(12) United States Patent
Hodgkinson et al.

(10) Patent No.: US 11,478,245 B2
(45) Date of Patent: Oct. 25, 2022

(54) SURGICAL STAPLING DEVICE

(71) Applicant: Covidien LP, Mansfield, MA (US)

(72) Inventors: Gerald N. Hodgkinson, Killingworth, CT (US); Michael A. Soltz, Fairfield, CT (US); Sulaiman Hussaini, Santa Rosa, CA (US); Souad Sedlik, Windsor, CA (US)

(73) Assignees: COVIDIEN LP, Mansfield, MA (US); MEDTRONIC, INC., Minneapolis, MN (US)

( * ) Notice: Subject to any disclaimer, the term of this patent is extended or adjusted under 35 U.S.C. 154(b) by 126 days.

(21) Appl. No.: 16/839,332

(22) Filed: Apr. 3, 2020

(65) Prior Publication Data
US 2020/0352571 A1 Nov. 12, 2020

Related U.S. Application Data

(60) Provisional application No. 62/844,870, filed on May 8, 2019.

(51) Int. Cl.
*A61B 17/072* (2006.01)
*A61B 17/00* (2006.01)
(Continued)

(52) U.S. Cl.
CPC ...... *A61B 17/07292* (2013.01); *A61K 9/0024* (2013.01); *A61K 45/06* (2013.01);
(Continued)

(58) Field of Classification Search
CPC ............ A61B 17/072; A61B 17/07207; A61B 17/07292; A61B 2017/00818;
(Continued)

(56) References Cited

U.S. PATENT DOCUMENTS 3,054,406 A 9/1962 Usher
3,124,136 A 3/1964 Usher
(Continued)

FOREIGN PATENT DOCUMENTS

CA 2282761 A1 9/1998
DE 1602563 U 3/1950
(Continued)

OTHER PUBLICATIONS

TAB—Definition, by Merriam-Webster Dictionary. Retrieved from URL https://www.merriam-webster.com/dictionary/tab on Feb. 1, 2022 (Year: 2022).*
(Continued)

*Primary Examiner* — Valentin Neacsu
(74) *Attorney, Agent, or Firm* — Carter, DeLuca & Farrell LLP

(57) ABSTRACT

Surgical stapling apparatuses have a buttress attached thereto. The buttress includes an elongate rectangular body having a proximal portion, a distal portion, and opposing lateral sides running along the elongate rectangular body from the proximal portion to the distal portion. The buttress possesses a layer of a therapeutic agent on at least the proximal portion. In embodiments the buttress possesses the therapeutic agent at both the proximal portion and the distal portion.

19 Claims, 5 Drawing Sheets

(51) Int. Cl.
*A61K 9/00* (2006.01)
*A61K 45/06* (2006.01)

(52) U.S. Cl.
CPC .............. *A61B 2017/00818* (2013.01); *A61B 2017/00893* (2013.01); *A61B 2017/07257* (2013.01); *A61B 2017/07271* (2013.01)

(58) Field of Classification Search
CPC ........... A61B 2017/00893; A61B 2017/07257; A61B 2017/07271; A61B 2017/07214; A61B 2017/07285; A61K 45/06
USPC ......... 227/176.1, 175.1, 180.1, 19, 901, 902
See application file for complete search history.

(56) References Cited

U.S. PATENT DOCUMENTS

| | | |
|---|---|---|
| 3,364,200 A | 1/1968 | Ashton et al. |
| 3,499,591 A | 3/1970 | Green |
| 3,797,494 A | 3/1974 | Zaffaroni |
| 3,939,068 A | 2/1976 | Wendt et al. |
| 3,948,666 A | 4/1976 | Kitanishi et al. |
| 4,064,062 A | 12/1977 | Yurko |
| 4,166,800 A | 9/1979 | Fong |
| 4,282,236 A | 8/1981 | Broom |
| 4,347,847 A | 9/1982 | Usher |
| 4,354,628 A | 10/1982 | Green |
| 4,416,698 A | 11/1983 | McCorsley, III |
| 4,429,695 A | 2/1984 | Green |
| 4,452,245 A | 6/1984 | Usher |
| 4,605,730 A | 8/1986 | Shalaby et al. |
| 4,626,253 A | 12/1986 | Broadnax, Jr. |
| 4,655,221 A | 4/1987 | Devereux |
| 4,834,090 A | 5/1989 | Moore |
| 4,838,884 A | 6/1989 | Dumican et al. |
| 4,927,640 A | 5/1990 | Dahlinder et al. |
| 4,930,674 A | 6/1990 | Barak |
| 5,002,551 A | 3/1991 | Linsky et al. |
| 5,014,899 A | 5/1991 | Presty et al. |
| 5,040,715 A | 8/1991 | Green et al. |
| 5,057,334 A | 10/1991 | Vail |
| 5,065,929 A | 11/1991 | Schulze et al. |
| 5,112,496 A | 5/1992 | Dhawan et al. |
| 5,162,430 A | 11/1992 | Rhee et al. |
| 5,205,459 A | 4/1993 | Brinkerhoff et al. |
| 5,263,629 A | 11/1993 | Trumbull et al. |
| 5,281,197 A | 1/1994 | Arias et al. |
| 5,307,976 A | 5/1994 | Olson et al. |
| 5,312,023 A | 5/1994 | Green et al. |
| 5,314,471 A | 5/1994 | Brauker et al. |
| 5,318,221 A | 6/1994 | Green et al. |
| 5,324,775 A | 6/1994 | Rhee et al. |
| 5,326,013 A | 7/1994 | Green et al. |
| 5,332,142 A | 7/1994 | Robinson et al. |
| 5,344,454 A | 9/1994 | Clarke et al. |
| 5,392,979 A | 2/1995 | Green et al. |
| 5,397,324 A | 3/1995 | Carroll et al. |
| 5,405,072 A | 4/1995 | Zlock et al. |
| 5,410,016 A | 4/1995 | Hubbell et al. |
| 5,425,745 A | 6/1995 | Green et al. |
| 5,441,193 A | 8/1995 | Gravener |
| 5,441,507 A | 8/1995 | Wilk |
| 5,443,198 A | 8/1995 | Viola et al. |
| 5,468,253 A | 11/1995 | Bezwada et al. |
| 5,484,913 A | 1/1996 | Stilwell et al. |
| 5,503,638 A | 4/1996 | Cooper et al. |
| 5,514,379 A | 5/1996 | Weissleder et al. |
| 5,542,594 A | 8/1996 | McKean et al. |
| 5,543,441 A | 8/1996 | Rhee et al. |
| 5,549,628 A | 8/1996 | Cooper et al. |
| 5,550,187 A | 8/1996 | Rhee et al. |
| 5,575,803 A | 11/1996 | Cooper et al. |
| 5,645,915 A | 7/1997 | Kranzler et al. |
| 5,653,756 A | 8/1997 | Clarke et al. |
| 5,683,809 A | 11/1997 | Freeman et al. |
| 5,690,675 A | 11/1997 | Sawyer et al. |
| 5,702,409 A | 12/1997 | Rayburn et al. |
| 5,752,965 A | 5/1998 | Francis et al. |
| 5,752,974 A | 5/1998 | Rhee et al. |
| 5,762,256 A | 6/1998 | Mastri et al. |
| 5,766,188 A | 6/1998 | Igaki |
| 5,769,892 A | 6/1998 | Kingwell |
| 5,782,396 A | 7/1998 | Mastri et al. |
| 5,799,857 A | 9/1998 | Robertson et al. |
| 5,810,855 A | 9/1998 | Rayburn et al. |
| 5,814,057 A | 9/1998 | Oi et al. |
| 5,819,350 A | 10/1998 | Wang |
| 5,833,695 A | 11/1998 | Yoon |
| 5,843,096 A | 12/1998 | Igaki et al. |
| 5,871,135 A | 2/1999 | Williamson IV et al. |
| 5,874,500 A | 2/1999 | Rhee et al. |
| 5,895,412 A | 4/1999 | Tucker |
| 5,895,415 A | 4/1999 | Chow et al. |
| 5,902,312 A | 5/1999 | Frater et al. |
| 5,908,427 A | 6/1999 | McKean et al. |
| 5,915,616 A | 6/1999 | Viola et al. |
| 5,931,847 A | 8/1999 | Bittner et al. |
| 5,957,363 A | 9/1999 | Heck |
| 5,964,774 A | 10/1999 | McKean et al. |
| 5,997,895 A | 12/1999 | Narotam et al. |
| 6,019,791 A | 2/2000 | Wood |
| 6,030,392 A | 2/2000 | Dakov |
| 6,032,849 A | 3/2000 | Mastri et al. |
| 6,045,560 A | 4/2000 | McKean et al. |
| 6,063,097 A | 5/2000 | Oi et al. |
| 6,080,169 A | 6/2000 | Turtel |
| 6,093,557 A | 7/2000 | Pui et al. |
| 6,099,551 A | 8/2000 | Gabbay |
| 6,142,933 A | 11/2000 | Longo et al. |
| 6,149,667 A | 11/2000 | Hovland et al. |
| 6,152,943 A | 11/2000 | Sawhney |
| 6,155,265 A | 12/2000 | Hammerslag |
| 6,156,677 A | 12/2000 | Brown Reed et al. |
| 6,165,201 A | 12/2000 | Sawhney et al. |
| 6,179,862 B1 | 1/2001 | Sawhney |
| 6,210,439 B1 | 4/2001 | Firmin et al. |
| 6,214,020 B1 | 4/2001 | Mulhauser et al. |
| 6,241,139 B1 | 6/2001 | Milliman et al. |
| 6,258,107 B1 | 7/2001 | Balazs et al. |
| 6,267,772 B1 | 7/2001 | Mulhauser et al. |
| 6,270,530 B1 | 8/2001 | Eldridge et al. |
| 6,273,897 B1 | 8/2001 | Dalessandro et al. |
| 6,280,453 B1 | 8/2001 | Kugel et al. |
| 6,299,631 B1 | 10/2001 | Shalaby |
| 6,309,569 B1 | 10/2001 | Farrar et al. |
| 6,312,457 B1 | 11/2001 | DiMatteo et al. |
| 6,312,474 B1 | 11/2001 | Francis et al. |
| 6,325,810 B1 | 12/2001 | Hamilton et al. |
| 6,399,362 B1 | 6/2002 | Pui et al. |
| 6,436,030 B2 | 8/2002 | Rehil |
| 6,454,780 B1 | 9/2002 | Wallace |
| 6,461,368 B2 | 10/2002 | Fogarty et al. |
| 6,500,777 B1 | 12/2002 | Wiseman et al. |
| 6,503,257 B2 | 1/2003 | Grant et al. |
| 6,514,283 B2 | 2/2003 | DiMatteo et al. |
| 6,514,534 B1 | 2/2003 | Sawhney |
| 6,517,566 B1 | 2/2003 | Hovland et al. |
| 6,551,356 B2 | 4/2003 | Rousseau |
| 6,566,406 B1 | 5/2003 | Pathak et al. |
| 6,568,398 B2 | 5/2003 | Cohen |
| 6,590,095 B1 | 7/2003 | Schleicher et al. |
| 6,592,597 B2 | 7/2003 | Grant et al. |
| 6,605,294 B2 | 8/2003 | Sawhney |
| 6,610,006 B1 | 8/2003 | Amid et al. |
| 6,627,749 B1 | 9/2003 | Kumar |
| 6,638,285 B2 | 10/2003 | Gabbay |
| 6,652,594 B2 | 11/2003 | Francis et al. |
| 6,656,193 B2 | 12/2003 | Grant et al. |
| 6,656,200 B2 | 12/2003 | Li et al. |
| 6,669,735 B1 | 12/2003 | Pelissier |
| 6,673,093 B1 | 1/2004 | Sawhney |
| 6,677,258 B2 | 1/2004 | Carroll et al. |
| 6,685,714 B2 | 2/2004 | Rousseau |
| 6,702,828 B2 | 3/2004 | Whayne |

(56) References Cited

U.S. PATENT DOCUMENTS

| | | |
|---|---|---|
| 6,703,047 B2 | 3/2004 | Sawhney et al. |
| 6,704,210 B1 | 3/2004 | Myers |
| 6,723,114 B2 | 4/2004 | Shalaby |
| 6,726,706 B2 | 4/2004 | Dominguez |
| 6,736,823 B2 | 5/2004 | Darois et al. |
| 6,736,854 B2 | 5/2004 | Vadurro et al. |
| 6,746,458 B1 | 6/2004 | Cloud |
| 6,746,869 B2 | 6/2004 | Pui et al. |
| 6,764,720 B2 | 7/2004 | Pui et al. |
| 6,773,458 B1 | 8/2004 | Brauker et al. |
| 6,818,018 B1 | 11/2004 | Sawhney |
| 6,843,252 B2 | 1/2005 | Harrison et al. |
| 6,896,684 B2 | 5/2005 | Monassevitch et al. |
| 6,927,315 B1 | 8/2005 | Heinecke et al. |
| 6,939,358 B2 | 9/2005 | Palacios et al. |
| 6,946,196 B2 | 9/2005 | Foss |
| 6,953,139 B2 | 10/2005 | Milliman et al. |
| 6,959,851 B2 | 11/2005 | Heinrich |
| 7,009,034 B2 | 3/2006 | Pathak et al. |
| 7,025,772 B2 | 4/2006 | Gellman et al. |
| 7,060,087 B2 | 6/2006 | DiMatteo et al. |
| 7,087,065 B2 | 8/2006 | Ulmsten et al. |
| 7,108,701 B2 | 9/2006 | Evens et al. |
| 7,128,253 B2 | 10/2006 | Mastri et al. |
| 7,128,748 B2 | 10/2006 | Mooradian et al. |
| 7,134,438 B2 | 11/2006 | Makower et al. |
| 7,141,055 B2 | 11/2006 | Abrams et al. |
| 7,147,138 B2 | 12/2006 | Shelton, IV |
| 7,160,299 B2 | 1/2007 | Baily |
| 7,179,268 B2 | 2/2007 | Roy et al. |
| 7,210,810 B1 | 5/2007 | Iversen et al. |
| 7,214,727 B2 | 5/2007 | Kwon et al. |
| 7,232,449 B2 | 6/2007 | Sharkawy et al. |
| 7,241,300 B2 | 7/2007 | Sharkawy et al. |
| 7,247,338 B2 | 7/2007 | Pui et al. |
| 7,279,322 B2 | 10/2007 | Pui et al. |
| 7,307,031 B2 | 12/2007 | Carroll et al. |
| 7,308,998 B2 | 12/2007 | Mastri et al. |
| 7,311,720 B2 | 12/2007 | Mueller et al. |
| 7,328,829 B2 | 2/2008 | Arad et al. |
| 7,347,850 B2 | 3/2008 | Sawhney |
| 7,377,928 B2 | 5/2008 | Zubik et al. |
| 7,434,717 B2 | 10/2008 | Shelton, IV et al. |
| 7,438,209 B1 | 10/2008 | Hess et al. |
| 7,464,849 B2 | 12/2008 | Shelton, IV et al. |
| 7,498,063 B2 | 3/2009 | Pui et al. |
| 7,547,312 B2 | 6/2009 | Bauman et al. |
| 7,559,937 B2 | 7/2009 | de la Torre et al. |
| 7,571,845 B2 | 8/2009 | Viola |
| 7,592,418 B2 | 9/2009 | Pathak et al. |
| 7,594,921 B2 | 9/2009 | Browning |
| 7,595,392 B2 | 9/2009 | Kumar et al. |
| 7,604,151 B2 | 10/2009 | Hess et al. |
| 7,611,494 B2 | 11/2009 | Campbell et al. |
| 7,635,073 B2 | 12/2009 | Heinrich |
| 7,645,874 B2 | 1/2010 | Saferstein et al. |
| 7,649,089 B2 | 1/2010 | Kumar et al. |
| 7,655,288 B2 | 2/2010 | Bauman et al. |
| 7,662,409 B2 | 2/2010 | Masters |
| 7,662,801 B2 | 2/2010 | Kumar et al. |
| 7,665,646 B2 | 2/2010 | Prommersberger |
| 7,666,198 B2 | 2/2010 | Suyker et al. |
| 7,669,747 B2 | 3/2010 | Weisenburgh, II et al. |
| 7,673,782 B2 | 3/2010 | Hess et al. |
| 7,708,180 B2 | 5/2010 | Murray et al. |
| 7,709,631 B2 | 5/2010 | Harris et al. |
| 7,717,313 B2 | 5/2010 | Criscuolo et al. |
| 7,722,642 B2 | 5/2010 | Williamson, IV et al. |
| 7,735,703 B2 | 6/2010 | Morgan et al. |
| 7,744,627 B2 | 6/2010 | Orban, III et al. |
| 7,754,002 B2 | 7/2010 | Maase et al. |
| 7,776,060 B2 | 8/2010 | Mooradian et al. |
| 7,789,889 B2 | 9/2010 | Zubik et al. |
| 7,793,813 B2 | 9/2010 | Bettuchi |
| 7,799,026 B2 | 9/2010 | Schechter et al. |
| 7,823,592 B2 | 11/2010 | Bettuchi et al. |
| 7,824,420 B2 | 11/2010 | Eldridge et al. |
| 7,845,533 B2 | 12/2010 | Marczyk et al. |
| 7,845,536 B2 | 12/2010 | Viola et al. |
| 7,846,149 B2 | 12/2010 | Jankowski |
| 7,892,247 B2 | 2/2011 | Conston et al. |
| 7,909,224 B2 | 3/2011 | Prommersberger |
| 7,909,837 B2 | 3/2011 | Crews et al. |
| 7,938,307 B2 | 5/2011 | Bettuchi |
| 7,942,890 B2 | 5/2011 | D'Agostino et al. |
| 7,950,561 B2 | 5/2011 | Aranyi |
| 7,951,166 B2 | 5/2011 | Orban, III et al. |
| 7,951,248 B1 | 5/2011 | Fallis et al. |
| 7,967,179 B2 | 6/2011 | Olson et al. |
| 7,988,027 B2 | 8/2011 | Olson et al. |
| 8,011,550 B2 | 9/2011 | Aranyi et al. |
| 8,011,555 B2 | 9/2011 | Tarinelli et al. |
| 8,016,177 B2 | 9/2011 | Bettuchi et al. |
| 8,016,178 B2 | 9/2011 | Olson et al. |
| 8,025,199 B2 | 9/2011 | Whitman et al. |
| 8,028,883 B2 | 10/2011 | Stopek |
| 8,033,483 B2 | 10/2011 | Fortier et al. |
| 8,033,983 B2 | 10/2011 | Chu et al. |
| 8,038,045 B2 | 10/2011 | Bettuchi et al. |
| 8,062,330 B2 | 11/2011 | Prommersberger et al. |
| 8,062,673 B2 | 11/2011 | Figuly et al. |
| 8,083,119 B2 | 12/2011 | Prommersberger |
| 8,091,756 B2 | 1/2012 | Viola |
| 8,123,766 B2 | 2/2012 | Bauman et al. |
| 8,123,767 B2 | 2/2012 | Bauman et al. |
| 8,127,975 B2 | 3/2012 | Olson et al. |
| 8,133,336 B2 | 3/2012 | Kettlewell et al. |
| 8,133,559 B2 | 3/2012 | Lee et al. |
| 8,146,791 B2 | 4/2012 | Bettuchi et al. |
| 8,152,777 B2 | 4/2012 | Campbell et al. |
| 8,157,149 B2 | 4/2012 | Olson et al. |
| 8,157,151 B2 | 4/2012 | Ingmanson et al. |
| 8,167,895 B2 | 5/2012 | D'Agostino et al. |
| 8,177,797 B2 | 5/2012 | Shimoji et al. |
| 8,178,746 B2 | 5/2012 | Hildeberg et al. |
| 8,192,460 B2 | 6/2012 | Orban, III et al. |
| 8,201,720 B2 | 6/2012 | Hessler |
| 8,210,414 B2 | 7/2012 | Bettuchi et al. |
| 8,210,453 B2 | 7/2012 | Hull et al. |
| 8,225,799 B2 | 7/2012 | Bettuchi |
| 8,225,981 B2 | 7/2012 | Criscuolo et al. |
| 8,231,043 B2 | 7/2012 | Tarinelli et al. |
| 8,235,273 B2 | 8/2012 | Olson et al. |
| 8,245,901 B2 | 8/2012 | Stopek |
| 8,252,339 B2 | 8/2012 | Figuly et al. |
| 8,252,921 B2 | 8/2012 | Vignon et al. |
| 8,256,654 B2 | 9/2012 | Bettuchi et al. |
| 8,257,391 B2 | 9/2012 | Orban, III et al. |
| 8,276,800 B2 | 10/2012 | Bettuchi |
| 8,286,849 B2 | 10/2012 | Bettuchi |
| 8,308,042 B2 | 11/2012 | Aranyi |
| 8,308,045 B2 | 11/2012 | Bettuchi et al. |
| 8,308,046 B2 | 11/2012 | Prommersberger |
| 8,312,885 B2 | 11/2012 | Bettuchi et al. |
| 8,313,014 B2 | 11/2012 | Bettuchi |
| 8,317,790 B2 | 11/2012 | Bell et al. |
| 8,322,590 B2 | 12/2012 | Patel et al. |
| 8,348,126 B2 | 1/2013 | Olson et al. |
| 8,348,130 B2 * | 1/2013 | Shah ............... A61B 17/07207 227/180.1 |
| 8,365,972 B2 | 2/2013 | Aranyi et al. |
| 8,367,089 B2 | 2/2013 | Wan et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,372,094 B2 | 2/2013 | Bettuchi et al. |
| 8,393,514 B2 | 3/2013 | Shelton, IV et al. |
| 8,393,517 B2 | 3/2013 | Milo |
| 8,408,440 B2 | 4/2013 | Olson et al. |
| 8,408,480 B2 | 4/2013 | Hull et al. |
| 8,413,869 B2 | 4/2013 | Heinrich |
| 8,413,871 B2 | 4/2013 | Racenet et al. |
| 8,418,909 B2 | 4/2013 | Kostrzewski |
| 8,424,742 B2 | 4/2013 | Bettuchi |

(56) References Cited

U.S. PATENT DOCUMENTS

| | | |
|---|---|---|
| 8,449,603 B2 | 5/2013 | Weber et al. |
| 8,453,652 B2 | 6/2013 | Stopek |
| 8,453,904 B2 | 6/2013 | Eskaros et al. |
| 8,453,909 B2 | 6/2013 | Olson et al. |
| 8,453,910 B2 | 6/2013 | Bettuchi et al. |
| 8,464,925 B2 | 6/2013 | Hull et al. |
| 8,470,360 B2 | 6/2013 | McKay |
| 8,474,677 B2 | 7/2013 | Woodard, Jr. et al. |
| 8,479,968 B2 | 7/2013 | Hodgkinson et al. |
| 8,485,414 B2 | 7/2013 | Criscuolo et al. |
| 8,496,683 B2 | 7/2013 | Prommersberger et al. |
| 8,511,533 B2 | 8/2013 | Viola et al. |
| 8,512,402 B2 | 8/2013 | Marczyk et al. |
| 8,518,440 B2 | 8/2013 | Blaskovich et al. |
| 8,529,600 B2 | 9/2013 | Woodard, Jr. et al. |
| 8,540,128 B2 | 9/2013 | Shelton, IV et al. |
| 8,540,131 B2 | 9/2013 | Swayze |
| 8,551,138 B2 | 10/2013 | Orban, III et al. |
| 8,556,918 B2 | 10/2013 | Bauman et al. |
| 8,561,873 B2 * | 10/2013 | Ingmanson .......... A61B 17/072 227/176.1 |
| 8,579,990 B2 | 11/2013 | Priewe |
| 8,584,920 B2 | 11/2013 | Hodgkinson |
| 8,590,762 B2 | 11/2013 | Hess et al. |
| 8,616,430 B2 | 12/2013 | (Prommersberger) Stopek et al. |
| 8,617,132 B2 | 12/2013 | Golzarian et al. |
| 8,631,989 B2 | 1/2014 | Aranyi et al. |
| 8,646,674 B2 | 2/2014 | Schulte et al. |
| 8,668,129 B2 | 3/2014 | Olson |
| 8,678,263 B2 | 3/2014 | Viola |
| 8,679,137 B2 | 3/2014 | Bauman et al. |
| 8,684,250 B2 | 4/2014 | Bettuchi et al. |
| 8,701,958 B2 | 4/2014 | Shelton, IV et al. |
| 8,721,703 B2 | 5/2014 | Fowler |
| 8,727,197 B2 | 5/2014 | Hess et al. |
| 8,757,466 B2 | 6/2014 | Olson et al. |
| 8,789,737 B2 | 7/2014 | Hodgkinson et al. |
| 8,814,888 B2 | 8/2014 | Sgro |
| 8,820,606 B2 | 9/2014 | Hodgkinson |
| 8,827,133 B2 | 9/2014 | Shelton, IV et al. |
| 8,857,694 B2 | 10/2014 | Shelton, IV et al. |
| 8,864,009 B2 | 10/2014 | Shelton, IV et al. |
| 8,870,050 B2 | 10/2014 | Hodgkinson |
| 8,900,616 B2 | 12/2014 | Belcheva et al. |
| 8,920,443 B2 * | 12/2014 | Hiles ................. A61B 17/0643 606/151 |
| 8,920,444 B2 | 12/2014 | Hiles et al. |
| 8,939,344 B2 | 1/2015 | Olson et al. |
| 8,956,390 B2 * | 2/2015 | Shah ............... A61B 17/07207 606/219 |
| 8,967,448 B2 | 3/2015 | Carter et al. |
| 9,005,243 B2 | 4/2015 | Stopek et al. |
| 9,010,606 B2 | 4/2015 | Aranyi et al. |
| 9,010,608 B2 | 4/2015 | Casasanta, Jr. et al. |
| 9,010,609 B2 | 4/2015 | Carter et al. |
| 9,010,610 B2 | 4/2015 | Hodgkinson |
| 9,010,612 B2 | 4/2015 | Stevenson et al. |
| 9,016,543 B2 | 4/2015 | (Prommersberger) Stopek et al. |
| 9,016,544 B2 | 4/2015 | Hodgkinson et al. |
| 9,027,817 B2 | 5/2015 | Milliman et al. |
| 9,044,227 B2 | 6/2015 | Shelton, IV et al. |
| 9,055,944 B2 | 6/2015 | Hodgkinson et al. |
| 9,084,602 B2 | 7/2015 | Gleiman |
| 9,107,665 B2 | 8/2015 | Hodgkinson et al. |
| 9,107,667 B2 | 8/2015 | Hodgkinson |
| 9,113,871 B2 | 8/2015 | Milliman et al. |
| 9,113,873 B2 | 8/2015 | Marczyk et al. |
| 9,113,885 B2 | 8/2015 | Hodgkinson et al. |
| 9,113,893 B2 | 8/2015 | Sorrentino et al. |
| 9,161,753 B2 | 10/2015 | Prior |
| 9,161,757 B2 | 10/2015 | Bettuchi |
| 9,186,140 B2 | 11/2015 | Hiles et al. |
| 9,186,144 B2 | 11/2015 | Stevenson et al. |
| 9,192,378 B2 | 11/2015 | Aranyi et al. |
| 9,192,379 B2 | 11/2015 | Aranyi et al. |
| 9,192,380 B2 | 11/2015 | (Tarinelli) Racenet et al. |
| 9,192,383 B2 | 11/2015 | Milliman |
| 9,192,384 B2 | 11/2015 | Bettuchi |
| 9,198,660 B2 | 12/2015 | Hodgkinson |
| 9,198,663 B1 | 12/2015 | Marczyk et al. |
| 9,204,881 B2 | 12/2015 | Penna |
| 9,220,504 B2 | 12/2015 | Viola et al. |
| 9,226,754 B2 | 1/2016 | D'Agostino et al. |
| 9,237,892 B2 | 1/2016 | Hodgkinson |
| 9,237,893 B2 | 1/2016 | Carter et al. |
| 9,277,922 B2 | 3/2016 | Carter et al. |
| 9,295,466 B2 | 3/2016 | Hodgkinson et al. |
| 9,326,768 B2 | 5/2016 | Shelton, IV |
| 9,326,773 B2 | 5/2016 | Casasanta, Jr. et al. |
| 9,328,111 B2 | 5/2016 | Zhou et al. |
| 9,345,479 B2 | 5/2016 | (Tarinelli) Racenet et al. |
| 9,351,729 B2 | 5/2016 | Orban, III et al. |
| 9,351,731 B2 | 5/2016 | Carter et al. |
| 9,351,732 B2 | 5/2016 | Hodgkinson |
| 9,358,005 B2 | 6/2016 | Shelton, IV et al. |
| 9,364,229 B2 | 6/2016 | D'Agostino et al. |
| 9,364,234 B2 | 6/2016 | (Prommersberger) Stopek et al. |
| 9,386,988 B2 | 7/2016 | Baxter, III et al. |
| 9,402,627 B2 | 8/2016 | Stevenson et al. |
| 9,414,839 B2 | 8/2016 | Penna |
| 9,433,412 B2 | 9/2016 | Bettuchi et al. |
| 9,433,413 B2 | 9/2016 | Stopek |
| 9,433,420 B2 | 9/2016 | Hodgkinson |
| 9,445,812 B2 | 9/2016 | Olson et al. |
| 9,445,817 B2 | 9/2016 | Bettuchi |
| 9,463,260 B2 | 10/2016 | Stopek |
| 9,486,215 B2 | 11/2016 | Olson et al. |
| 9,492,170 B2 | 11/2016 | Bear et al. |
| 9,504,470 B2 | 11/2016 | Milliman |
| 9,517,164 B2 | 12/2016 | Vitaris et al. |
| 9,572,576 B2 | 2/2017 | Hodgkinson et al. |
| 9,585,657 B2 | 3/2017 | Shelton, IV et al. |
| 9,597,077 B2 | 3/2017 | Hodgkinson |
| 9,610,080 B2 | 4/2017 | Whitfield et al. |
| 9,622,745 B2 | 4/2017 | Ingmanson et al. |
| 9,629,626 B2 * | 4/2017 | Soltz .................. A61B 17/072 |
| 9,636,850 B2 | 5/2017 | Stopek (nee Prommersberger) et al. |
| 9,655,620 B2 | 5/2017 | Prescott et al. |
| 9,675,351 B2 | 6/2017 | Hodgkinson et al. |
| 9,681,936 B2 | 6/2017 | Hodgkinson et al. |
| 9,687,262 B2 | 6/2017 | Rousseau et al. |
| 9,693,772 B2 | 7/2017 | Ingmanson et al. |
| 9,708,184 B2 | 7/2017 | Chan et al. |
| 9,770,245 B2 | 9/2017 | Swayze et al. |
| 9,775,617 B2 | 10/2017 | Carter et al. |
| 9,782,173 B2 | 10/2017 | Mozdzierz |
| 10,245,034 B2 * | 4/2019 | Shelton, IV ...... A61B 17/07292 |
| 10,806,459 B2 * | 10/2020 | Hodgkinson ....... A61B 17/1155 |
| 10,874,768 B2 * | 12/2020 | Morgan ................ A61L 31/041 |
| 10,888,530 B2 * | 1/2021 | Schwartz ............... A61L 27/54 |
| 2002/0091397 A1 | 7/2002 | Chen |
| 2002/0151911 A1 | 10/2002 | Gabbay |
| 2003/0065345 A1 | 4/2003 | Weadock |
| 2003/0078209 A1 | 4/2003 | Schmidt |
| 2003/0083676 A1 | 5/2003 | Wallace |
| 2003/0125676 A1 | 7/2003 | Swenson et al. |
| 2003/0181927 A1 | 9/2003 | Wallace |
| 2003/0183671 A1 * | 10/2003 | Mooradian .......... A61B 17/115 227/175.1 |
| 2003/0208231 A1 | 11/2003 | Williamson et al. |
| 2004/0092912 A1 | 5/2004 | Jinno et al. |
| 2004/0107006 A1 | 6/2004 | Francis et al. |
| 2004/0254590 A1 | 12/2004 | Hoffman et al. |
| 2004/0260272 A1 | 12/2004 | Friedman et al. |
| 2004/0260315 A1 | 12/2004 | Dell et al. |
| 2005/0002981 A1 | 1/2005 | Lahtinen et al. |
| 2005/0006429 A1 | 1/2005 | Wales et al. |
| 2005/0021085 A1 | 1/2005 | Abrams et al. |
| 2005/0059996 A1 * | 3/2005 | Bauman ................ A61B 17/115 606/215 |
| 2005/0059997 A1 * | 3/2005 | Bauman ................ A61B 17/115 606/219 |
| 2005/0070929 A1 | 3/2005 | Dalessandro et al. |

(56) References Cited

U.S. PATENT DOCUMENTS

| | | |
|---|---|---|
| 2005/0118435 A1 | 6/2005 | DeLucia et al. |
| 2005/0149073 A1 | 7/2005 | Arani et al. |
| 2005/0283256 A1 | 12/2005 | Sommerich et al. |
| 2006/0004407 A1* | 1/2006 | Hiles .................. A61B 17/0644 606/215 |
| 2006/0008505 A1 | 1/2006 | Brandon |
| 2006/0121266 A1 | 6/2006 | Fandel et al. |
| 2006/0173470 A1 | 8/2006 | Oray et al. |
| 2006/0190027 A1 | 8/2006 | Downey |
| 2007/0034669 A1 | 2/2007 | de la Torre et al. |
| 2007/0179528 A1* | 8/2007 | Soltz .................. A61B 17/07207 606/219 |
| 2007/0203510 A1 | 8/2007 | Bettuchi |
| 2007/0212394 A1 | 9/2007 | Reyes et al. |
| 2007/0224235 A1 | 9/2007 | Tenney et al. |
| 2007/0243227 A1 | 10/2007 | Gertner |
| 2007/0246505 A1 | 10/2007 | Pace-Floridia et al. |
| 2008/0009811 A1 | 1/2008 | Cantor |
| 2008/0029570 A1 | 2/2008 | Shelton et al. |
| 2008/0082126 A1 | 4/2008 | Murray et al. |
| 2008/0140115 A1 | 6/2008 | Stopek |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0216855 A1 | 9/2008 | Nasca |
| 2008/0220047 A1 | 9/2008 | Sawhney et al. |
| 2008/0286325 A1 | 11/2008 | Reyes et al. |
| 2008/0290134 A1 | 11/2008 | Bettuchi et al. |
| 2009/0001121 A1 | 1/2009 | Hess et al. |
| 2009/0001130 A1 | 1/2009 | Hess et al. |
| 2009/0031842 A1 | 2/2009 | Kawai et al. |
| 2009/0206125 A1 | 8/2009 | Huitema et al. |
| 2009/0206126 A1 | 8/2009 | Huitema et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0218384 A1 | 9/2009 | Aranyi |
| 2009/0277944 A9 | 11/2009 | Dalessandro et al. |
| 2010/0016855 A1 | 1/2010 | Ramstein et al. |
| 2010/0016888 A1 | 1/2010 | Calabrese et al. |
| 2010/0076489 A1 | 3/2010 | Stopek et al. |
| 2010/0087840 A1 | 4/2010 | Ebersole et al. |
| 2010/0147921 A1 | 6/2010 | Olson |
| 2010/0147922 A1 | 6/2010 | Olson |
| 2010/0174253 A1 | 7/2010 | Cline et al. |
| 2010/0203151 A1 | 8/2010 | Hiraoka |
| 2010/0243707 A1 | 9/2010 | Olson et al. |
| 2010/0331859 A1 | 12/2010 | Omori |
| 2011/0034910 A1 | 2/2011 | Ross et al. |
| 2011/0087279 A1* | 4/2011 | Shah .................. A61B 17/07207 606/219 |
| 2011/0089220 A1 | 4/2011 | Ingmanson et al. |
| 2011/0125138 A1 | 5/2011 | Malinouskas et al. |
| 2011/0166673 A1 | 7/2011 | Patel et al. |
| 2011/0293690 A1 | 12/2011 | Griffin et al. |
| 2011/0295200 A1 | 12/2011 | Speck et al. |
| 2012/0080336 A1 | 4/2012 | Shelton, IV et al. |
| 2012/0125792 A1* | 5/2012 | Cassivi .................. A61N 5/1027 206/205 |
| 2012/0145767 A1* | 6/2012 | Shah .................. A61B 17/07292 227/180.1 |
| 2012/0168486 A1* | 7/2012 | Ingmanson .......... A61B 17/068 227/176.1 |
| 2012/0171383 A1 | 7/2012 | Christensen et al. |
| 2012/0197272 A1 | 8/2012 | Oray et al. |
| 2012/0241491 A1 | 9/2012 | Aldridge et al. |
| 2012/0241493 A1 | 9/2012 | Baxter, III et al. |
| 2012/0253298 A1 | 10/2012 | Henderson et al. |
| 2012/0316633 A1 | 12/2012 | Flanagan et al. |
| 2013/0146643 A1* | 6/2013 | Schmid .............. A61B 17/0686 227/180.1 |
| 2013/0153636 A1 | 6/2013 | Shelton, IV et al. |
| 2013/0153641 A1 | 6/2013 | Shelton, IV et al. |
| 2013/0209659 A1 | 8/2013 | Racenet et al. |
| 2013/0256380 A1 | 10/2013 | Schmid et al. |
| 2014/0048580 A1 | 2/2014 | Merchant et al. |
| 2014/0131418 A1 | 5/2014 | Kostrzewski |
| 2014/0239047 A1 | 8/2014 | Hodgkinson et al. |
| 2015/0041347 A1 | 2/2015 | Hodgkinson |
| 2015/0133995 A1 | 5/2015 | Shelton, IV et al. |
| 2015/0209045 A1 | 7/2015 | Hodgkinson et al. |
| 2015/0305743 A1 | 10/2015 | Casasanta et al. |
| 2015/0327864 A1 | 11/2015 | Hodgkinson et al. |
| 2016/0022268 A1 | 1/2016 | Prior |
| 2016/0045200 A1 | 2/2016 | Milliman |
| 2016/0100834 A1 | 4/2016 | Viola et al. |
| 2016/0106430 A1 | 4/2016 | Carter et al. |
| 2016/0157857 A1 | 6/2016 | Hodgkinson et al. |
| 2016/0174988 A1 | 6/2016 | D'Agostino et al. |
| 2016/0206315 A1 | 7/2016 | Olson |
| 2016/0220257 A1 | 8/2016 | Casasanta et al. |
| 2016/0249923 A1 | 9/2016 | Hodgkinson et al. |
| 2016/0250013 A1* | 9/2016 | Skalla .................. A61L 31/10 600/37 |
| 2016/0256166 A1 | 9/2016 | (Prommersberger) Stopek et al. |
| 2016/0270793 A1 | 9/2016 | Carter et al. |
| 2016/0310143 A1 | 10/2016 | Bettuchi |
| 2016/0317720 A1 | 11/2016 | Ostapoff et al. |
| 2016/0338704 A1 | 11/2016 | Penna |
| 2016/0367252 A1 | 12/2016 | Dlson et al. |
| 2016/0367253 A1 | 12/2016 | Hodgkinson |
| 2016/0367257 A1 | 12/2016 | Stevenson et al. |
| 2017/0042540 A1 | 2/2017 | Olson et al. |
| 2017/0049452 A1 | 2/2017 | Milliman |
| 2017/0055986 A1* | 3/2017 | Harris ................ A61B 17/1155 |
| 2017/0055989 A1* | 3/2017 | Shelton, IV .......... A61B 17/00 |
| 2017/0056546 A1* | 3/2017 | Shelton, IV .......... A61L 17/005 |
| 2017/0150967 A1 | 6/2017 | Hodgkinson et al. |
| 2017/0172720 A1* | 6/2017 | Schwartz .............. A61F 2/0063 |
| 2017/0281182 A1* | 10/2017 | Nativ .................. A61B 17/1114 |
| 2017/0303923 A1* | 10/2017 | Scheib ................ A61B 17/105 |
| 2017/0303926 A1* | 10/2017 | Scheib ............ A61B 17/07207 |
| 2018/0193282 A1* | 7/2018 | Schwartz ................ A61L 31/10 |
| 2018/0207321 A1* | 7/2018 | Morgan .................. A61L 27/56 |
| 2018/0256164 A1* | 9/2018 | Aranyi ................ A61B 17/072 |
| 2019/0021730 A1* | 1/2019 | Hodgkinson .......... A61L 27/54 |
| 2020/0085440 A1* | 3/2020 | Hodgkinson ...... A61B 17/1155 |
| 2020/0138729 A1* | 5/2020 | Schwartz .............. A61L 31/148 |
| 2020/0352565 A1* | 11/2020 | Schulz-Jander ... A61B 17/0686 |
| 2020/0352570 A1* | 11/2020 | Hussaini .................. A61L 31/16 |
| 2020/0397443 A1* | 12/2020 | Hodgkinson .... A61B 17/07292 |

FOREIGN PATENT DOCUMENTS

| | | |
|---|---|---|
| DE | 19924311 A1 | 11/2000 |
| EP | 0327022 A2 | 8/1989 |
| EP | 0594148 A1 | 4/1994 |
| EP | 3087931 A2 | 11/2016 |
| EP | 3431111 A1 | 1/2019 |
| JP | 2000166933 A | 6/2000 |
| JP | 2002202213 A | 7/2002 |
| JP | 2007124166 A | 5/2007 |
| JP | 2010214132 A | 9/2010 |
| WO | 9005489 A1 | 5/1990 |
| WO | 95/16221 A1 | 6/1995 |
| WO | 98/38923 A1 | 9/1998 |
| WO | 9926826 A2 | 6/1999 |
| WO | 0010456 A1 | 3/2000 |
| WO | 0016684 A1 | 3/2000 |
| WO | 2010021757 A2 | 2/2010 |
| WO | 2010075298 A2 | 7/2010 |
| WO | 2015137962 A1 | 9/2015 |
| WO | 2016205652 A1 | 12/2016 |
| WO | 2017046193 A1 | 3/2017 |

OTHER PUBLICATIONS

Extended European Search Report corresponding to EP 14 16 9739.1, completed Aug. 19, 2014 and dated Aug. 29, 2014; (7 pp).

Extended European Search Report corresponding to EP 14 15 7997.9, completed Sep. 9, 2014 and dated Sep. 17, 2014; (8 pp).

(56) References Cited

OTHER PUBLICATIONS

Extended European Search Report corresponding to EP 14 16 8904.2, completed Sep. 10, 2014 and dated Sep. 18, 2014; (8 pp).
Extended European Search Report corresponding to EP 13 19 4995.0, completed Jun. 5, 2014 and dated Oct. 13, 2014; (10 pp).
Extended European Search Report corresponding to EP 13 15 4571.7, completed Oct. 10, 2014 and dated Oct. 20, 2014; (8 pp).
Extended European Search Report corresponding to EP 14 18 1125.7, completed Oct. 16, 2014 and dated Oct. 24, 2014; (7 pp).
Extended European Search Report corresponding to EP 14 18 1127.3, completed Oct. 16, 2014 and dated Nov. 10, 2014; (8 pp).
Extended European Search Report corresponding to EP 14 19 0419.3, completed Mar. 24, 2015 and dated Mar. 30, 2015; (6 pp).
European Office Action corresponding to EP 12 198 776.2 dated Apr. 7, 2015.
European Office Action corresponding to EP 13 156 297.7 dated Apr. 10, 2015.
Australian Examination Report No. 1 corresponding to AU 2011250822 dated May 18, 2015.
European Office Action corresponding to EP 12 186 175.1 dated Jun. 1, 2015.
Chinese Office Action corresponding to CN 201010517292.8 dated Jun. 2, 2015.
Extended European Search Report corresponding to EP 14 17 4814.5 dated Jun. 9, 2015.
Australian Examination Report No. 1 corresponding to AU 2014200584 dated Jun. 15, 2015.
European Office Action corresponding to EP 13 180 881.8 dated Jun. 19, 2015.
European Office Action corresponding to EP 14 157 195.0 dated Jul. 2, 2015.
Extended European Search Report corresponding to EP 12 19 6902.6 dated Aug. 6, 2015.
Extended European Search Report corresponding to EP 14 15 2060.1 dated Aug. 14, 2015.
Chinese Office Action corresponding to CN 201210129787.2 dated Aug. 24, 2015.
Canadian Office Action corresponding to CA 2,665,206 dated Nov. 19, 2013.
Chinese Notification of Reexamination corresponding to CN 201010517292.8 dated Jun. 2, 2015.
Japanese Office Action corresponding to JP 2014-216989 dated Sep. 11, 2015.
Canadian First Office Action corresponding to CA 2,686,105 dated Sep. 17, 2015.
Japanese Office Action corresponding to JP 2012-040188 dated Oct. 21, 2015.
European Communication corresponding to EP 13 17 6895.4 dated Nov. 5, 2015.
Chinese First Office Action corresponding to CN 201210544552 dated Nov. 23, 2015.
Chinese First Office Action corresponding to CN 201210545228 dated Nov. 30, 2015.
Extended European Search Report corresponding to EP 15 18 0491.1 dated Dec. 9, 2015.
Extended European Search Report corresponding to EP 15 18 3819.0 dated Dec. 11, 2015.
Canadian Office Action corresponding to CA 2,697,819 dated Jan. 6, 2016.
Canadian Office Action corresponding to CA 2,696,419 dated Jan. 14, 2016.
European Office Action corresponding to EP 12 19 8776.2 dated Jan. 19, 2016.
Extended European Search Report corresponding to EP 15 17 4146.9 dated Jan. 20, 2016.
Chinese First Office Action corresponding to CN 201310353628.5 dated Jan. 25, 2016.
Extended European Search Report corresponding to EP 12 19 6912.5 dated Feb. 1, 2016.
Japanese Office Action corresponding to JP 2012-098903 dated Feb. 22, 2016.
Extended European Search Report corresponding to EP 12 19 8753.1 dated Feb. 24, 2016.
Chinese First Office Action corresponding to CN 201410449019.4 dated Mar. 30, 2016.
Extended European Search Report corresponding to EP 16 15 0232.3 dated Apr. 12, 2016.
European Office Action corresponding to EP 11 18 3256.4 dated Apr. 20, 2016.
Australian Examination Report No. 1 corresponding to AU 2012244169 dated May 10, 2016.
European Office Action corresponding to EP 10 25 0715.9 dated May 12, 2016.
Chinese First Office Action corresponding to CN 201410778512.0 dated May 13, 2016.
Australian Examination Report No. 1 corresponding to AU 2012227358 dated May 16, 2016.
Japanese Office Action corresponding to JP 2012-040188 dated May 17, 2016.
Australian Examination Report No. 1 corresponding to AU 2012244380 dated May 20, 2016.
Australian Examination Report No. 1 corresponding to AU 2014227480 dated May 21, 2016.
Australian Examination Report No. 1 corresponding to AU 2012254977 dated May 30, 2016.
European Search Report corresponding to EP 06 00 4598, completed Jun. 22, 2006; (2 pp).
European Search Report corresponding to EP 06 01 6962.0, completed Jan. 3, 2007 and dated Jan. 11, 2007; (10 pp).
International Search Report corresponding to International Application No. PCT/US2005/036740, completed Feb. 20, 2007 and dated Mar. 23, 2007; (8 pp).
International Search Report corresponding to International Application No. PCT/US2007/022713, completed Apr. 21, 2008 and dated May 15, 2008; (1 p).
International Search Report corresponding to International Application No. PCT/US2008/002981, completed Jun. 9, 2008 and dated Jun. 26, 2008; (2 pp).
European Search Report corresponding to EP 08 25 1779, completed Jul. 14, 2008 and dated Jul. 23, 2008 (5 pp).
European Search Report corresponding to EP 08 25 1989.3, completed Mar. 11, 2010 and dated Mar. 24, 2010; (6 pp).
European Search Report corresponding to EP 10 25 0639.1, completed Jun. 17, 2010 and dated Jun. 28, 2010; (7 pp).
European Search Report corresponding to EP 10 25 0715.9, completed Jun. 30, 2010 and dated Jul. 20, 2010; (3 pp).
European Search Report corresponding to EP 05 80 4382.9, completed Oct. 5, 2010 and dated Oct. 12, 2010; (3 pp).
European Search Report corresponding to EP 09 25 2897.5, completed Feb. 7, 2011 and dated Feb. 15, 2011; (3 pp).
European Search Report corresponding to EP 10 25 0642.5, completed Mar. 25, 2011 and dated Apr. 4, 2011; (4 pp).
European Search Report corresponding to EP 12 15 2229.6, completed Feb. 23, 2012 and dated Mar. 1, 2012; (4 pp).
European Search Report corresponding to EP 12 15 0511.9, completed Apr. 16, 2012 and dated Apr. 24, 2012; (7 pp).
European Search Report corresponding to EP 12 15 2541.4, completed Apr. 23, 2012 and dated May 3, 2012; (10 pp).
European Search Report corresponding to EP 12 16 5609.4, completed Jul. 5, 2012 and dated Jul. 13, 2012; (8 pp).
European Search Report corresponding to EP 12 15 8861.0, completed Jul. 17, 2012 and dated Jul. 24, 2012; (9 pp).
European Search Report corresponding to EP 12 16 5878.5, completed Jul. 24, 2012 and dated Aug. 6, 2012; (8 pp).
Extended European Search Report corresponding to EP 12 19 1035.0, completed Jan. 11, 2013 and dated Jan. 18, 2013; (7 pp).
Extended European Search Report corresponding to EP 12 18 6175.1, completed Jan. 15, 2013 and dated Jan. 23, 2013; (7 pp).
Extended European Search Report corresponding to EP 12 19 1114.3, completed Jan. 23, 2013 and dated Jan. 31, 2013; (10 pp).
Extended European Search Report corresponding to EP 12 19 2224.9, completed Mar. 14, 2013 and dated Mar. 26, 2013; (8 pp).

(56) References Cited

OTHER PUBLICATIONS

Extended European Search Report corresponding to EP 12 19 6904.2, completed Mar. 28, 2013 and dated Jul. 26, 2013; (8 pp).
Extended European Search Report corresponding to EP 12 19 6911.7, completed Apr. 18, 2013 and dated Apr. 24, 2013; (8 pp).
Extended European Search Report corresponding to EP 07 00 5842.5, completed May 13, 2013 and dated May 29, 2013; (7 pp).
Extended European Search Report corresponding to EP 12 19 8776.2, completed May 16, 2013 and dated May 27, 2013; (8 pp).
Extended European Search Report corresponding to EP 12 19 8749.9, completed May 21, 2013 and dated May 31, 2013; (8 pp).
Extended European Search Report corresponding to EP 13 15 6297.7, completed Jun. 4, 2013 and dated Jun. 13, 2013; (7 pp).
Extended European Search Report corresponding to EP 13 17 3985.6, completed Aug. 19, 2013 and dated Aug. 28, 2013; (6 pp).
Extended European Search Report corresponding to EP 13 17 3986.4, completed Aug. 20, 2013 and dated Aug. 29, 2013; (6 pp).
Extended European Search Report corresponding to EP 13 17 7437.4, completed Sep. 11, 2013 and dated Sep. 19, 2013; 6 pages.
Extended European Search Report corresponding to EP 13 17 7441.6, completed Sep. 11, 2013 and dated Sep. 19, 2013; (6 pp).
Extended European Search Report corresponding to EP 07 86 1534.1, completed Sep. 20, 2013 and dated Sep. 30, 2013; (5 pp).
Extended European Search Report corresponding to EP 13 18 3876.5, completed Oct. 14, 2013 and dated Oct. 24, 2013; (5 pp).
Extended European Search Report corresponding to EP 13 17 1856.1, completed Oct. 29, 2013 and dated Nov. 7, 2013; (8 pp).
Extended European Search Report corresponding to EP 13 18 0373.6, completed Oct. 31, 2013 and dated Nov. 13, 2013; (7 pp).
Extended European Search Report corresponding to EP 13 18 0881.8, completed Nov. 5, 2013 and dated Nov. 14, 2013; (6 pp).
Extended European Search Report corresponding to EP 13 17 6895.4, completed Nov. 29, 2013 and dated Dec. 12, 2013; (5 pp).
Extended European Search Report corresponding to EP 13 18 2911.1, completed Dec. 2, 2013 and dated Dec. 16, 2013; (8 pp).
Extended European Search Report corresponding to EP 10 25 1795.0, completed Dec. 11, 2013 and dated Dec. 20, 2013; (6 pp).
Extended European Search Report corresponding to EP 13 18 7911.6, completed Jan. 22, 2014 and dated Jan. 31, 2014; (8 pp).
Extended European Search Report corresponding to EP 13 19 2111.6, completed Feb. 13, 2014 and dated Feb. 27, 2014; (10 pp).
Extended European Search Report corresponding to EP 13 19 5919.9, completed Feb. 10, 2014 and dated Mar. 3, 2014; (7 pp).
Extended European Search Report corresponding to EP 08 72 6500.5, completed Feb. 20, 2014 and dated Mar. 3, 2014; (7 pp).
Extended European Search Report corresponding to EP 13 19 5019.8, completed Mar. 14, 2014 and dated Mar. 24, 2014; (7 pp).
Extended European Search Report corresponding to EP 13 19 6816.6, completed Mar. 28, 2014 and dated Apr. 9, 2014; (9 pp).
Extended European Search Report corresponding to EP 13 19 7958.5, completed Apr. 4, 2014 and dated Apr. 15, 2014; (8 pp).
Extended European Search Report corresponding to EP 13 19 4995.0, completed Jun. 5, 2014 and dated Jun. 16, 2014; (5 pp).
Extended European Search Report corresponding to EP 14 15 7195.0, completed Jun. 5, 2014 and dated Jun. 18, 2014; (9 pp).
Extended European Search Report corresponding to EP 14 15 6342.9, completed Jul. 22, 2014 and dated Jul. 29, 2014; (8 pp).
European Office Action corresponding to EP 14 17 2681.0 dated May 13, 2016.
Extended European Search Report corresponding to EP 16 15 3647.9 dated Jun. 3, 2016.
Chinese Office Action corresponding to CN 201210545228 dated Jun. 29, 2016.
Japanese Office Action corresponding to JP 2012-250058 dated Jun. 29, 2016.
European Office Action corresponding to EP 14 15 7997.9 dated Jun. 29, 2016.
Canadian Office Action corresponding to CA 2,712,617 dated Jun. 30, 2016.
Chinese First Office Action corresponding to CN 2013103036903 dated Jun. 30, 2016.
Australian Patent Examination Report No. 1 corresponding to AU 2012250278 dated Jul. 10, 2016.
Australian Patent Examination Report No. 1 corresponding to AU 2012244382 dated Jul. 10, 2016.
Japanese Office Action corresponding to 2012-255242 dated Jul. 26, 2016.
Japanese Office Action corresponding to JP 2012-268668 dated Jul. 27, 2016.
European Office Action corresponding to EP 14 15 2060.1 dated Aug. 4, 2016.
European Office Action corresponding to EP 12 16 5609.4 dated Aug. 5, 2016.
European Office Action corresponding to EP 15 15 2392.5 dated Aug. 8, 2016.
Japanese Office Action corresponding to JP 2013-003624 dated Aug. 25, 2016.
Australian Patent Examination Report No. 1 corresponding to AU 2012261752 dated Sep. 6, 2016.
Japanese Office Action corresponding to JP 2014-252703 dated Sep. 26, 2016.
European Office Action corresponding to EP 12 19 8776.2 dated Sep. 12, 2016.
Japanese Office Action corresponding to JP 2013-000321 dated Sep. 13, 2016.
Chinese Second Office Action corresponding to CN 201310353628.5 dated Sep. 26, 2016.
European Office Action corresponding to EP 12 15 2541.4 dated Sep. 27, 2016.
Australian Patent Examination Report No. 1 corresponding to AU 2012268923 dated Sep. 28, 2016.
Chinese First Office Action corresponding to CN 2013107068710 dated Dec. 16, 2016.
Chinese First Office Action corresponding to CN 201310646606.8 dated Dec. 23, 2016.
Japanese Office Action corresponding to JP 2013-000321 dated Jan. 4, 2017.
Extended European Search Report corresponding to EP 16 16 6367.9 dated Jan. 16, 2017.
Australian Examination Report No. 1 corresponding to AU 2013206777 dated Feb. 1, 2017.
Chinese Second Office Action corresponding to CN 2013103036903 dated Feb. 23, 2017.
Japanese Office Action corresponding to JP 2013-175379 dated Mar. 1, 2017.
Chinese First Office Action corresponding to CN 201410028462.4 dated Mar. 2, 2017.
Chinese First Office Action corresponding to CN 201410084070 dated Mar. 13, 2017.
Extended European Search Report corresponding to EP 16 19 6549.6 dated Mar. 17, 2017.
Japanese Office Action corresponding to JP 2013-147701 dated Mar. 21, 2017.
Australian Examination Report No. 1 corresponding to AU 2013206804 dated Mar. 21, 2017.
Australian Examination Report No. 1 corresponding to AU 2013211499 dated May 4, 2017.
Australian Examination Report No. 1 corresponding to AU 2014201008 dated May 23, 2017.
Extended European Search Report issued in Appl. No. EP 18152491.9 dated Jun. 6, 2018 (12 pages).
Extended European Search Report issued in corresponding Appl. No. EP 18183850.9-1109 dated Dec. 20, 2018 (8 pages).
Extended European Search Report issued in corresponding Appl. No. EP 20172962.1 dated Sep. 18, 2020 (11 pages).

\* cited by examiner

SURGICAL STAPLING DEVICE

CROSS-REFERENCE TO RELATED APPLICATIONS

This application claims the benefit of the filing date of provisional U.S. Patent Application No. 62/844,870, filed May 8, 2019.

TECHNICAL FIELD

The present disclosure relates to medical devices, including surgical devices such as buttresses, for use with wound closure devices. Medical devices formed of the materials of the present disclosure are capable of delivering therapeutic agents to a patient.

BACKGROUND

Surgical stapling instruments are employed by surgeons to sequentially or simultaneously apply one or more rows of fasteners, e.g., staples or two-part fasteners, to body tissue for the purpose of joining segments of body tissue together. Such instruments generally include a pair of jaws or finger-like structures between which the body tissue to be joined is placed. When the stapling instrument is actuated, or "fired", longitudinally moving firing bars contact staple drive members in one of the jaws. The staple drive members push the surgical staples through the body tissue and into an anvil in the opposite jaw, which forms the staples. If tissue is to be removed or separated, a knife blade can be provided in the jaws of the device to cut the tissue between the lines of staples.

For some surgical procedures, it may be desirable to introduce therapeutic agents at the site of treatment.

Improved surgical repair materials, capable of use as buttresses for sealing and/or reinforcing staple lines against tissue, and improved methods for introducing therapeutic agents to a patient, remain desirable.

SUMMARY

The present disclosure relates to medical devices, including surgical stapling devices, which can be used to repair tissue.

A surgical stapling device of the present disclosure includes an end effector including an anvil jaw member and a cartridge assembly pivotally coupled to one another, the anvil jaw member and the cartridge jaw member being relatively movable such that the end effector is movable between an open position and a clamped position. In embodiments, a buttress is attached to the cartridge jaw member, the buttress having a distal portion and a proximal portion, at least one of the distal portion and the proximal portion having a therapeutic agent thereon.

In some embodiments, the therapeutic agent is applied as a coating to the distal portion of the buttress to form a first tab at the distal portion of the buttress, and the therapeutic agent is applied as a coating to the proximal portion of the buttress to form a second tab at the proximal portion of the buttress.

In other embodiments, a second buttress is attached to the anvil jaw member, the second buttress having a distal portion and a proximal portion, at least one of the distal portion and the proximal portion having a therapeutic agent thereon.

In embodiments, the therapeutic agent is applied as a coating to the distal portion of the second buttress to form a first tab at the distal portion of the second buttress, and the therapeutic agent is applied as a coating to the proximal portion of the second buttress to form a second tab at the proximal portion of the second buttress. In other embodiments, the therapeutic agent is applied as coating to the distal and/or proximal portions of the buttress such that the coating is not located where staples penetrate the buttress.

In some embodiments, the therapeutic agent is any combination of amino acids, peptides, polypeptides, proteins, polysaccharides, muteins, immunoglobulins, antibodies, cytokines, blood clotting factors, hemopoietic factors, interleukins (1 through 18), interferons, erythropoietin, nucleases, tumor necrosis factor, colony stimulating factors, insulin, anti-tumor agents and tumor suppressors, blood proteins, fibrin, thrombin, fibrinogen, synthetic thrombin, synthetic fibrin, synthetic fibrinogen, gonadotropins, hormones and hormone analogs, vaccines, somatostatin, antigens, blood coagulation factors, growth factors, bone morphogenic proteins, TGF-B, protein inhibitors, protein antagonists, protein agonists, nucleic acids, such as antisense molecules, DNA, RNA, RNAi, oligonucleotides, polynucleotides, cells, viruses, anti-inflammatory agents, anti-bacterial agents, antimicrobial agents, and ribozymes.

In other embodiments, the therapeutic agent is a chemotherapy drug. Suitable chemotherapy drugs include, for example, any combination of paclitaxel and derivatives thereof, docetaxel and derivatives thereof, abraxane, tamoxifen, cyclophosphamide, actinomycin, bleomycin, dactinomycin, daunorubicin, doxorubicin, doxorubicin hydrochloride, epirubicin, mitomycin, methotrexate, fluorouracil, gemcitabine, gemcitabine hydrochloride, carboplatin, carmustine, methyl-CCNU, cisplatin, etoposide, camptothecin and derivatives thereof, phenesterine, vinblastine, vincristine, goserelin, leuprolide, interferon alfa, retinoic acid, nitrogen mustard alkylating agents, piposulfan, vinorelbine, irinotecan, irinotecan hydrochloride, vinblastine, pemetrexed, sorafenib tosylate, everolimus, erlotinib hydrochloride, sunitinib malate, capecitabine oxaliplatin, leucovorin calcium, bevacizumab, cetuximab, ramucirumab, trastuzumab, atezolizumab, canakinumab, and combinations thereof.

In embodiments, the therapeutic agent is combined with an excipient including a surfactant/solubilizer, a salt, an acid, a stabilizer, a polyhydric alcohol, a hydrotrope, a low molecular weight poly(ethylene glycol) or any combination thereof.

Suitable surfactants include cyclodextrin, sodium dodecyl sulfate, octyl glucoside, a sorbitan fatty acid ester, or combinations thereof.

In some embodiments, the salt includes sodium chloride.

Suitable acids include oleic acid, citric acid, ascorbic acid, or combinations thereof.

In some embodiments, the stabilizer includes butylated hydroxytoluene or butylated hydroxyanisole.

In embodiments, the polyhydric alcohol includes D-sorbitol, mannitol, or combinations thereof.

In some embodiments, the buttress is attached to the cartridge jaw member by at least one suture.

In other embodiments, the second buttress is attached to the anvil jaw member by at least one suture.

In other embodiments, a surgical stapling device of the present disclosure includes an end effector including an anvil jaw member and a cartridge assembly pivotally coupled to one another, the anvil jaw member and the cartridge jaw member being relatively movable such that the end effector is movable between an open position and a clamped position. The surgical stapling device includes a buttress attached to the cartridge jaw member, the buttress having a distal portion and a proximal portion, at least one of the distal portion and the proximal portion having a chemotherapy drug thereon.

In some embodiments, the chemotherapy drug is applied as a coating to the distal portion of the buttress to form a first tab at the distal portion of the buttress, and the chemotherapy drug is applied as a coating to the proximal portion of the buttress to form a second tab at the proximal portion of the buttress.

In other embodiments, a second buttress is attached to the anvil jaw member, the second buttress having a distal portion and a proximal portion, at least one of the distal portion and the proximal portion having a chemotherapy drug thereon.

The chemotherapy drug may be applied as a coating to the distal portion of the second buttress to form a first tab at the distal portion of the second buttress, and the chemotherapy drug may be applied as a coating to the proximal portion of the second buttress to form a second tab at the proximal portion of the second buttress.

Methods for stapling tissue with the stapling device of the present disclosure are also provided.

BRIEF DESCRIPTION OF THE DRAWINGS

Embodiments of the presently disclosed surgical stapling device are described herein with reference to the drawings wherein.

DETAILED DESCRIPTION

Figure 1:
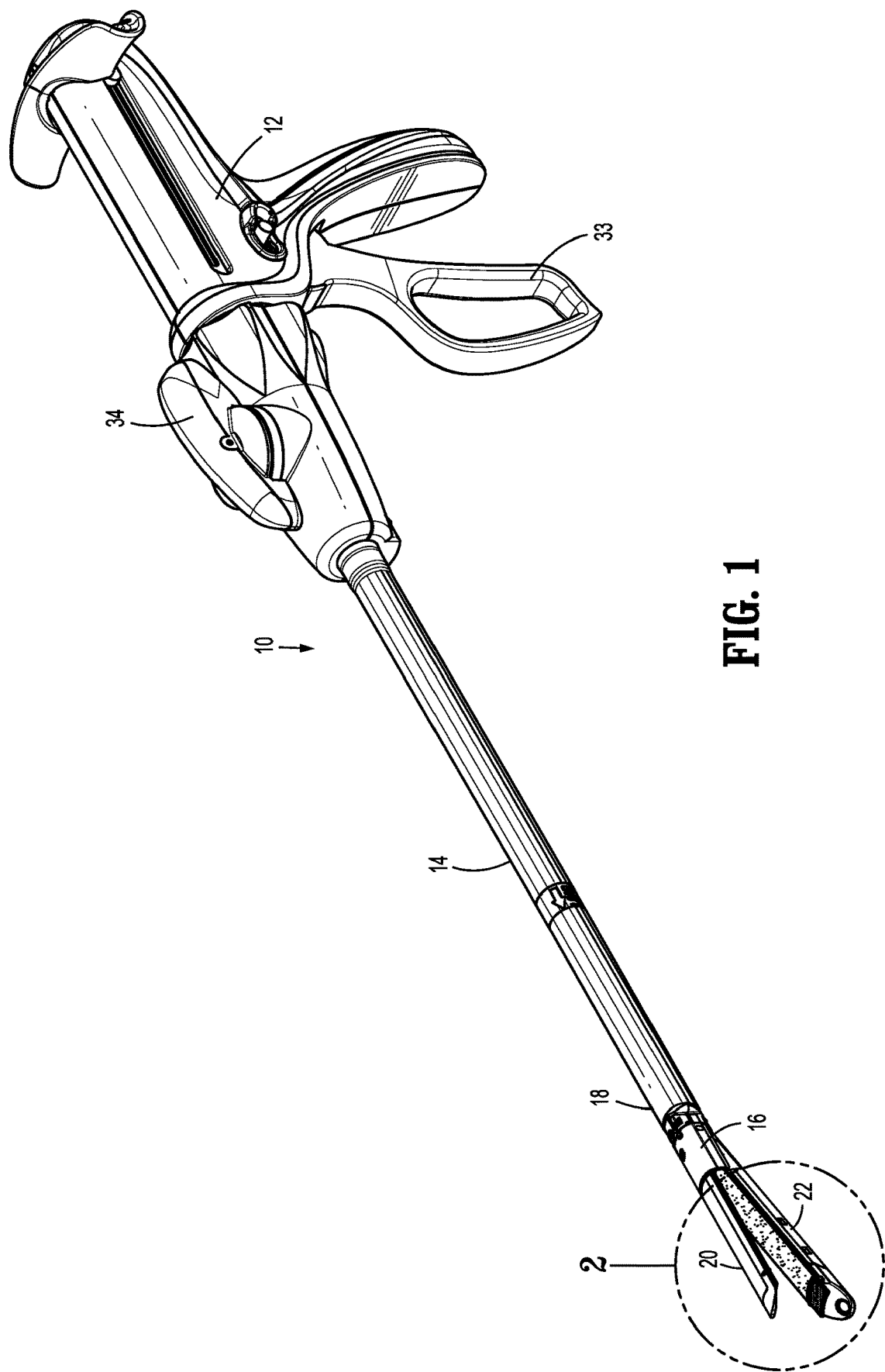
FIG. 1 is a perspective view of a surgical stapling apparatus including a handle housing, an adapter assembly, an end effector, and a buttress attached thereto in accordance with an embodiment of the present disclosure.

Various exemplary embodiments of the present disclosure are discussed herein below in terms of buttresses for use with tissue fixation devices, in embodiments surgical staples. While the below disclosure discusses in detail the use of these buttresses with staples, it will be appreciated that surgical buttresses of the present disclosure include a range of buttressing materials and film-based materials that may be used to mechanically support tissues, reinforce tissues along staple or suture lines, and decrease the incidence of fluid leakage and/or bleeding of tissues.

Surgical buttresses of the present disclosure may be used with any fixation device utilized to close any wound, defect, and/or opening in tissue. Thus, while surgical buttresses are discussed in conjunction with a surgical stapling apparatus, it is envisioned that other fixation devices, such as tacks, sutures, clips, adhesives, and the like, may be utilized in conjunction with surgical buttresses of the present disclosure to affix the medical devices to tissue.

The present disclosure provides a linear stapler buttress capable of delivering therapeutic agents both locally and regionally within a patient's body, which does not impede healing at the anastomotic site or within the staple line due to therapeutic agent coating colocalization with staple sites.

The surgical buttress of the present disclosure is in the form of a generally rectangular body having a distal end and a proximal end, with opposing lateral sides that run along the length of the elongate rectangular body portion from the distal end to the proximal end. The distal end and the proximal end of the surgical buttress, sometimes referred to herein as "tabs", has a therapeutic agent thereon. The tabs are in place to assist in the attachment of the pre-loaded buttress to the cartridge and/or anvil faces and remain at the end(s) of a staple line once the staples have been fired in tissue, attaching the buttress thereto.

Therapeutic agents included in therapeutic layers forming tab(s) on the surgical buttress of the present disclosure are suitable for further treatment of tissue at or near the site where the surgical buttress of the present disclosure is placed. Thus, the present disclosure describes surgical buttresses, and methods and mechanisms for using the same, for the targeted delivery of therapeutic agents to a patient.

The therapeutic agent may be patterned or applied as a unitary coating on the tabs. As the tabs are not incorporated into the staple line, in the case of double or triple stapling technique procedures, the multiple stapling of the tissue may transect and remove diseased tissue.

For colorectal and gastric procedures, therapeutic agent(s) from the buttress of the present disclosure may elute into the peritoneal cavity and travel through normal lymphatic drainage pathways to treat involved lymph nodes. For thoracic procedures, therapeutic agent(s) may be released near the anastomosis or other stapled sites and travel through normal lymphatic drainage pathways to treat involved lymph nodes. Where multiple staple lines are fired sequentially in a line with staple line ends overlapping, therapeutic agent(s) on only the distal or proximal buttress tabs would enable delivery of therapeutic agent(s) with each staple line without being incorporated into the stapled area of the staple line. Each of these embodiments provides the advantage that therapeutic agent coatings are displaced from the staple sites and thus pose less of a risk to staple line healing when compared with embodiments where a therapeutic agent is coated on the stapled area of the buttress.

It should be understood that a variety of surgical stapling apparatuses may be utilized with a surgical buttress of the present disclosure. For example, linear staplers may be utilized such as, for example, those including EndoGIA™ Reinforced Reload with Tri-Staple Technology™ and other staplers with Tri-Staple™ technology, available through Covidien, (North Haven, Conn.), as well as other anastomosis staplers, such as, for example, EEA™, CEEA™, GIA™, EndoGIA™, and TA™, also available through Covidien. It should also be appreciated that the principles of the present disclosure are equally applicable to surgical staplers having alternate configurations, such as, for example, end-to-end anastomosis staplers having a circular cartridge and anvil (see, e.g., commonly owned U.S. Pat. No. 5,915,616, entitled "Surgical Fastener Applying Apparatus," the entire disclosure of which is incorporated herein by this reference); laparoscopic staplers (see, e.g., commonly owned U.S. Pat. Nos. 6,330,965 and 6,241,139, each entitled "Surgical Stapling Apparatus," the entire disclosures of each of which are incorporated herein by this reference); and transverse anastomosis staplers (see, e.g., commonly owned U.S. Pat. Nos. 5,964,394 and 7,334,717, each entitled "Surgical Fastener Applying Apparatus", the entire disclosures of each of which are incorporated by reference herein).

Embodiments of the presently disclosed surgical buttress and surgical stapling apparatus will now be described in detail with reference to the drawing figures wherein like reference numerals identify similar or identical elements. In the following discussion, the terms "proximal" and "trailing" may be employed interchangeably, and should be understood as referring to the portion of a structure that is closer to a clinician during proper use. The terms "distal" and "leading" may also be employed interchangeably, and should be understood as referring to the portion of a structure that is further from the clinician during proper use. As used herein, the term "patient" should be understood as referring to a human subject or other animal, and the term "clinician" should be understood as referring to a doctor, nurse, or other care provider and may include support personnel.

Referring now to FIG. 1, there is disclosed an exemplary surgical stapling apparatus or surgical stapler 10 for use in stapling tissue and applying a surgical buttress to tissue. The surgical stapling apparatus 10 generally includes a handle 12 having an elongate tubular member 14 extending distally from the handle 12. An end effector 16 is mounted on a distal end 18 of the elongate tubular member 14. The end effector 16 includes an anvil assembly including a staple clinching anvil jaw member 20 and a cartridge assembly including a staple cartridge jaw member 22 configured to receive a staple cartridge 32. The end effector 16 may be permanently affixed to the elongate tubular member 14 or may be detachable and thus replaceable with a new end effector 16. The staple clinching anvil jaw member 20 is movably mounted on the distal end 18 of the end effector 16 and is movable between an open position spaced apart from the staple cartridge jaw member 22 to a closed position substantially adjacent the staple cartridge jaw member 22.

The surgical stapling apparatus 10 further includes a trigger 33, as seen in FIG. 1, movably mounted on the handle 12. Actuation of the trigger 33 initially operates to move the anvil jaw member 20 from the open to the closed position relative to the staple cartridge jaw member 22 and subsequently actuates the surgical stapling apparatus 10 to apply lines of staples to tissue. In order to properly orient the end effector 16 relative to the tissue to be stapled, the surgical stapling apparatus 10 is additionally provided with a rotation knob 34 mounted on the handle 12. Rotation of the rotation knob 34 relative to the handle 12 rotates the elongate tubular member 14 and the end effector 16 relative to the handle 12 so as to properly orient the end effector 16 relative to the tissue to be stapled.

Reference may be made to commonly owned U.S. Pat. Nos. 5,915,616, 6,330,965 and 6,241,139, the disclosures of each of which are incorporated by reference herein, for a detailed discussion of the construction and operation of surgical stapling apparatus 10.

Figure 2:
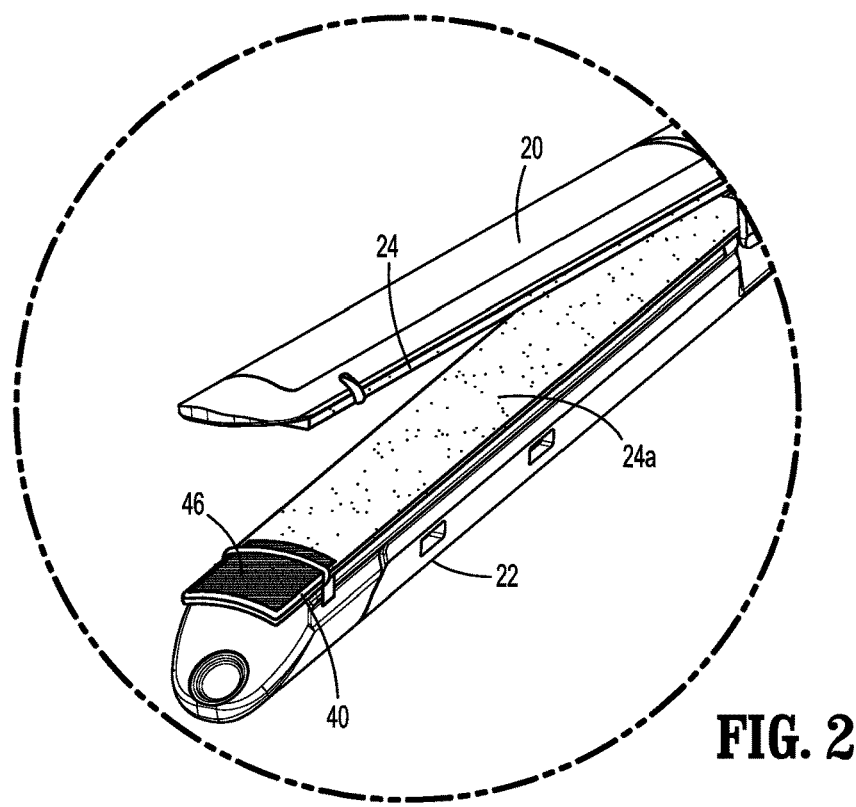
FIG. 2 is an enlarged view of the indicated area of detail shown in FIG. 1.
Figure 3:
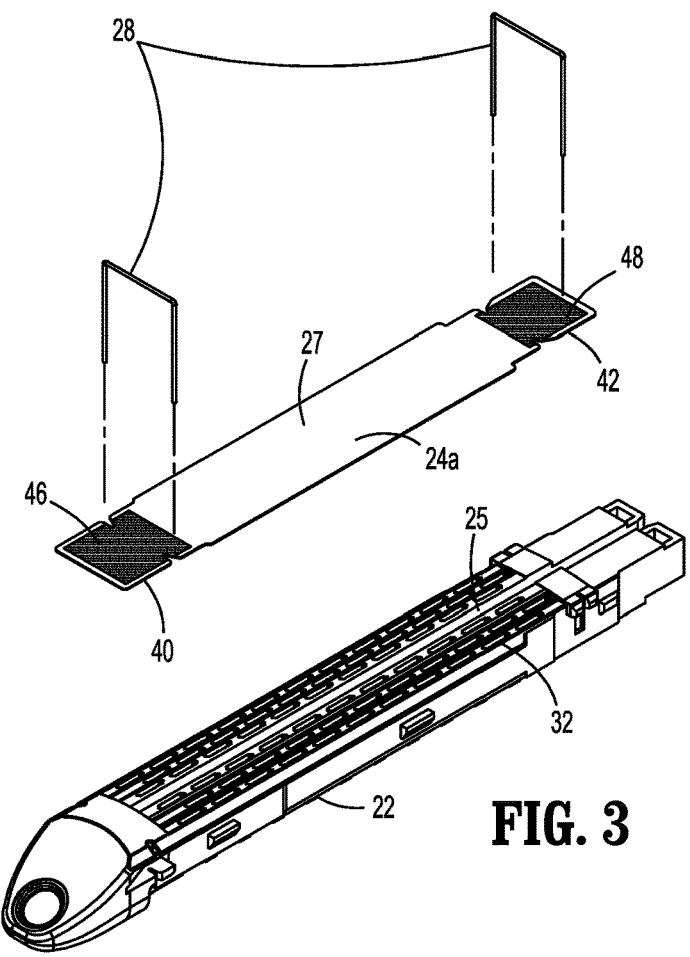
FIG. 3 is a perspective view of a cartridge assembly of the end effector of the surgical stapling apparatus shown in FIG. 1, showing how a buttress in accordance with an embodiment of the present disclosure may be attached thereto.

As depicted in FIGS. 2-3, the anvil jaw member 20 may be provided with a surgical buttress 24, and the staple cartridge jaw member 22 may be provided with a surgical buttress 24a. For ease of reference, the following description will focus on the surgical buttress 24a affixed to the staple cartridge jaw member 22, but it is to be understood that the surgical buttress 24 affixed to the anvil jaw member 20 may be formed of the same materials, having the same configuration and properties as the surgical buttress 24a affixed to the staple cartridge jaw member 22.

Figure 4:
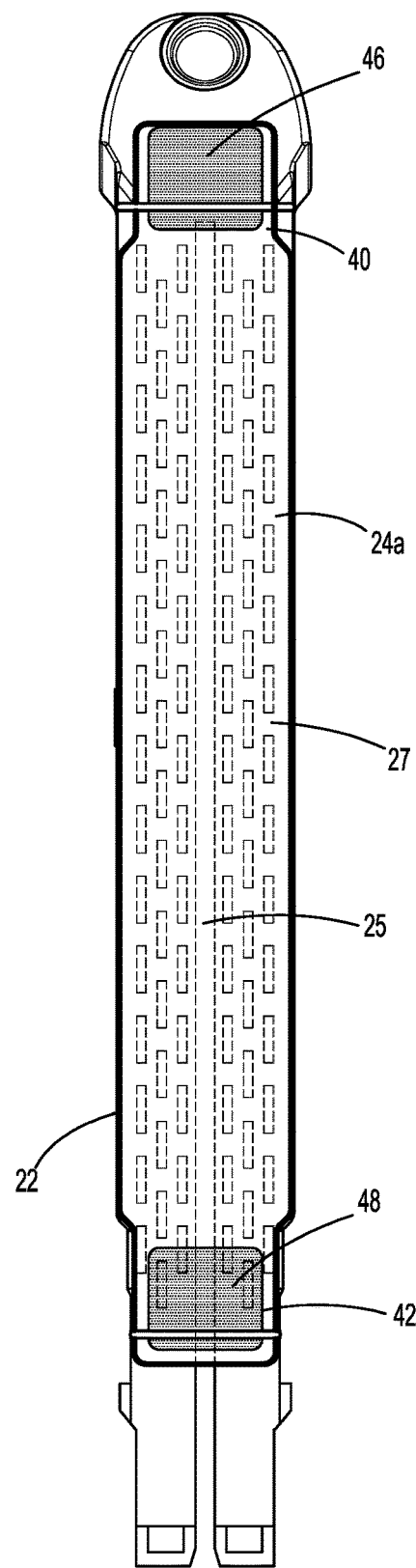
FIG. 4 is a top view of a cartridge assembly of the end effector of the surgical stapling apparatus shown in FIG. 3, showing the buttress attached thereto.

Referring to FIGS. 2-4, the staple cartridge jaw member 22 may be provided with a surgical buttress 24a. The surgical buttress 24a is provided to reinforce and seal staple lines applied to tissue by surgical stapling apparatus 10. The surgical buttress 24a may be configured in any shape, size, or dimension suitable to fit any surgical stapling, fastening, or firing apparatus. As illustrated in FIG. 3, the surgical buttress 24a may be attached to the cartridge jaw member 22 with sutures 28.

Upon full actuation of surgical stapling apparatus 10, a knife (not shown), disposed within knife slot 25 (FIG. 3) cuts tissue captured between the anvil jaw member 20 and the staple cartridge jaw member 22.

Surgical buttresses of the present disclosure may be fabricated from a biocompatible substrate material. Such substrates may be formed of bioabsorbable, non-absorbable, natural and/or synthetic materials.

In embodiments, the surgical buttress of the present disclosure may be biodegradable, so that the buttress does not have to be retrieved from the body. The term "biodegradable" as used herein is defined to include both bioabsorbable and bioresorbable materials. By biodegradable, it is meant that the surgical buttress decomposes or loses structural integrity under body conditions (e.g., enzymatic degradation or hydrolysis), or is broken down (physically or chemically) under physiologic conditions in the body such that the degradation products are excretable or absorbable by the body.

Non-limiting examples of materials which may be used in forming a surgical buttress of the present disclosure include, but are not limited to, poly(lactic acid), poly(glycolic acid), poly(trimethylene carbonate), poly(dioxanone), poly(hydroxybutyrate), poly(phosphazine), polyethylene terephthalate, polyethylene glycols, polyethylene oxides, polyacrylamides, polyhydroxyethylmethylacrylate, polyvinylpyrrolidone, polyvinyl alcohols, polyacrylic acid, polyacetate, polycaprolactone, polypropylene, aliphatic polyesters, glycerols, poly(amino acids), copoly(ether-esters), polyalkylene oxalates, polyamides, poly(iminocarbonates), polyalkylene oxalates, polyoxaesters, polyorthoesters, polyphosphazenes, and copolymers, block copolymers, homopolymers, blends and combinations thereof.

In embodiments, natural biological polymers may be used in forming a surgical buttress of the present disclosure. Suitable natural biological polymers include, but are not limited to, collagen, gelatin, fibrin, fibrinogen, elastin, keratin, albumin, cellulose, oxidized cellulose, hydroxyethyl cellulose, hydroxypropyl cellulose, carboxyethyl cellulose, carboxymethyl cellulose, chitin, chitosan, and combinations thereof. In addition, natural biological polymers may be combined with any of the other polymeric materials described herein to produce a surgical buttress of the present disclosure.

The surgical buttress may also be formed of materials that are porous or non-porous. It should of course be understood that any combination of porous, non-porous, natural, synthetic, bioabsorbable, and/or non-bioabsorbable materials may be used to form a surgical buttress of the present disclosure.

In some embodiments, a surgical buttress of the present disclosure may be formed of porous material(s). Any porous portion of a surgical buttress of the present disclosure may have openings or pores over at least a part of a surface thereof. Suitable porous materials include, but are not limited to, fibrous structures (e.g., knitted structures, woven structures, non-woven structures, etc.) and/or foams (e.g., open or closed cell foams).

In embodiments, the pores may be in sufficient number and size so as to interconnect across the entire thickness of the surgical buttress. Woven fabrics, knitted fabrics, non-woven fabrics and open cell foams are illustrative examples of structures in which the pores can be in sufficient number and size so as to interconnect across the entire thickness of the surgical buttress.

In other embodiments, the pores may not interconnect across the entire thickness of the surgical buttress. Closed cell foams or fused non-woven materials are illustrative examples of structures in which the pores may not interconnect across the entire thickness of the surgical buttress. In some embodiments, pores may be located on a portion of the surgical buttress, with other portions of the medical device having a non-porous texture. Those skilled in the art may envision a variety of pore distribution patterns and configurations for a porous medical device of the present disclosure.

Where the surgical buttress of the present disclosure is porous and includes fibrous materials, the surgical buttress may be formed using any suitable method including, but not limited to, knitting, weaving, non-woven techniques (including melt blowing, wet-spinning, electro-spinning, extrusion, co-extrusion, and the like. In embodiments, the surgical buttress possesses a three dimensional structure, such as the textiles described in U.S. Pat. Nos. 7,021,086 and 6,443,964, the entire disclosures of each of which are incorporated by reference herein.

The porosity of the fabric used to form the substrate may allow for the infiltration of biological fluids and/or cellular components which, in turn, may accelerate the release kinetics of any therapeutic agent from the surgical buttress of the present disclosure, thus increasing the rate of release of therapeutic agent(s) from the surgical buttress into the surrounding tissue and fluids.

Substrates used to form surgical buttresses of the present disclosure may have a thickness from about 0.05 mm to about 0.5 mm, in embodiments from about 0.1 mm to about 0.2 mm.

Where the substrate used to form the surgical buttress is porous, the surgical buttress of the present disclosure may have a pore volume from about 65% to about 85%, in embodiments from about 70% to about 80%.

As depicted in FIGS. 3-4, in embodiments, a surgical buttress 24a of the present disclosure may include an elongate rectangular body portion 27. The rectangular body portion 27 of the surgical buttress 24a has a distal portion 40 and a proximal portion 42. In some embodiments, the surgical buttress 24a of the present disclosure has a therapeutic agent at the distal portion 40, a therapeutic agent at the proximal portion 42, or both. The therapeutic agent may be incorporated within the materials used to form the distal portion 40 and the proximal portion 42 of the buttress 24a or, as depicted in FIGS. 3-4, the therapeutic agent may be applied as a coating thereby forming a first tab 46 at the distal portion 40 and a second tab 48 the proximal portion 42 of the buttress 24a.

While the above disclosure has been focused on surgical buttress 24a, it is to be understood that surgical buttress 24 may be of similar construction, possessing tabs 46a and 48a (FIG. 6) possessing a therapeutic agent at the distal portion and proximal portion thereof.

Figure 5:
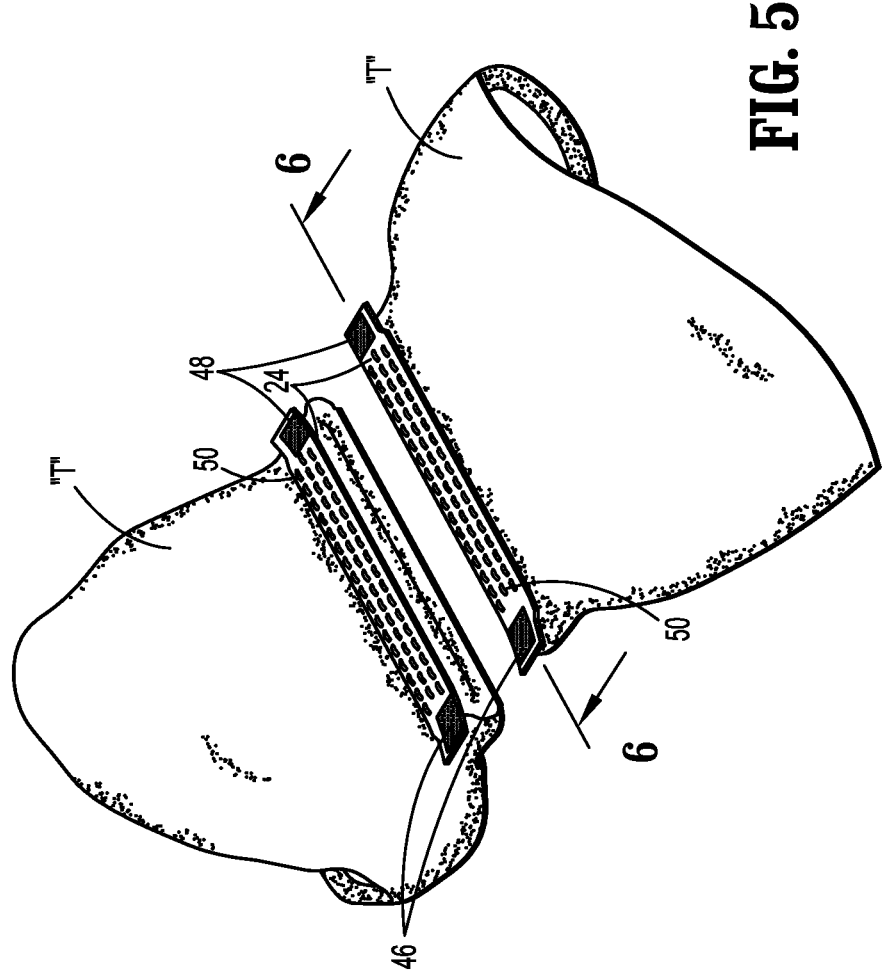
FIG. 5 is a perspective view of a stapled and divided section of tissue after firing of the surgical stapling apparatus of FIG. 1.
Figure 6:
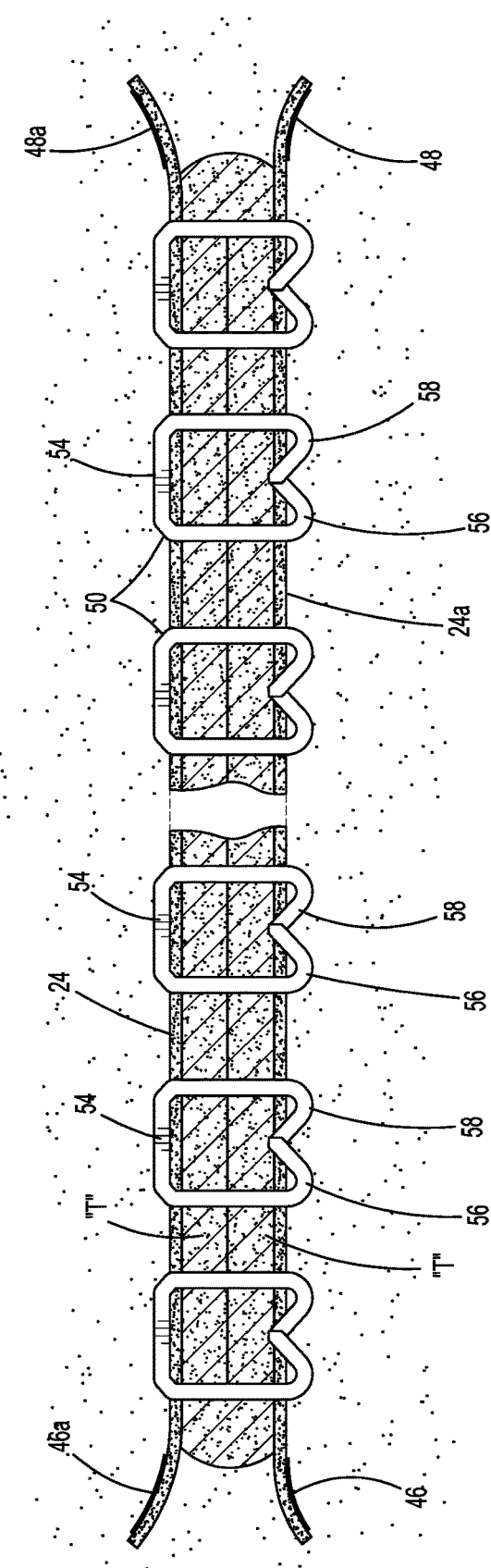
FIG. 6 is a side view of the stapled and divided section of tissue of FIG. 5, after firing of the surgical stapling apparatus of FIG. 1.

Turning to FIGS. 5-6, in embodiments the buttresses 24, 24a described herein may be used in sealing a wound by approximating the edges of wound tissue between the staple cartridge jaw member 22 and the anvil jaw member 20 of the surgical stapling apparatus. Firing of the surgical stapling apparatus 10 forces the staple legs 56, 58 of at least one staple 50 to pass through the openings on the staple cartridge jaw member 22, the buttress 24a on the staple cartridge jaw member 22, the tissue, the buttress 24 on the anvil jaw member 20, and the openings on the anvil (not shown) to secure the buttresses 24, 24a to the tissue so that the tissue is sandwiched between the two, thereby securing the adjoining tissue and to seal the tissue.

The resulting tissue "T", divided and stapled closed with staples 50, is illustrated in FIGS. 5-6. Specifically, the surgical buttress 24a that was associated with the staple cartridge jaw member 22 is secured against tissue "T" by backspans 54 of staples 50 and the surgical buttress 24 associated with the anvil jaw member 20 is secured against tissue "T" by staple legs 56 and 58. Thus, surgical buttresses 24, 24a are stapled to tissue "T" thereby sealing and reinforcing the staple lines created by staples 50.

As shown in FIG. 6, the tabs 46, 46a, 48, and 48a, having a therapeutic agent therein, are not incorporated in the staple line and are free of the stapled tissue.

While the above description is directed to rectangular buttresses, it is to be appreciated that any suitable configuration for a buttress may be utilized in accordance with the present disclosure. For example, buttresses having an elongate rectangular body with head and tail portions at the ends of the buttress may be utilized. For example, additional suitable buttresses include those disclosed in U.S. patent application Ser. No. 15/639,367, filed Jun. 30, 2017, and U.S. Pat. Nos. 8,157,151, 8,561,873 and 9,693,772, the entire disclosures of each of which are incorporated by reference herein.

Therapeutic agents which may be added to a surgical buttress of the present disclosure include, but are not limited to, drugs, amino acids, peptides, polypeptides, proteins, polysaccharides, muteins, immunoglobulins, antibodies, cytokines (e.g., lymphokines, monokines, chemokines), blood clotting factors, hemopoietic factors, interleukins (1 through 18), interferons ($\beta$-IFN, $\alpha$-IFN and $\gamma$-IFN), erythropoietin, nucleases, tumor necrosis factor, colony stimulating factors (e.g., GCSF, GM-CSF, MCSF), insulin, anti-tumor agents and tumor suppressors, blood proteins, fibrin, thrombin, fibrinogen, synthetic thrombin, synthetic fibrin, synthetic fibrinogen, gonadotropins (e.g., FSH, LH, CG, etc.), hormones and hormone analogs (e.g., growth hormone, luteinizing hormone releasing factor), vaccines (e.g., tumoral, bacterial and viral antigens), somatostatin, antigens, blood coagulation factors, growth factors (e.g., nerve growth factor, insulin-like growth factor), bone morphogenic proteins, TGF-B, protein inhibitors, protein antagonists, protein agonists, nucleic acids, such as antisense molecules, DNA, RNA, RNAi, oligonucleotides, polynucleotides, cells, viruses, anti-inflammatory agents, anti-bacterial agents, antimicrobial agents, and ribozymes.

In embodiments, the therapeutic agent applied to a surgical buttress of the present disclosure may include an anti-tumor agent and/or tumor suppressor, referred to, in embodiments, as a "chemotherapeutic agent" and/or an "antineoplastic agent." Suitable chemotherapeutic agents include, for example, paclitaxel and derivatives thereof, docetaxel and derivatives thereof, abraxane, tamoxifen, cyclophosphamide, actinomycin, bleomycin, dactinomycin, daunorubicin, doxorubicin, doxorubicin hydrochloride, epirubicin, mitomycin, methotrexate, fluorouracil, gemcitabine, gemcitabine hydrochloride, carboplatin, carmustine (BCNU), methyl-CCNU, cisplatin, etoposide, camptothecin and derivatives thereof, phenesterine, vinblastine, vincristine, goserelin, leuprolide, interferon alfa, retinoic acid (ATRA), nitrogen mustard alkylating agents, piposulfan, vinorelbine, irinotecan, irinotecan hydrochloride, vinblastine, pemetrexed, sorafenib tosylate, everolimus, erlotinib hydrochloride, sunitinib malate, capecitabine oxaliplatin, leucovorin calcium, bevacizumab, cetuximab, ramucirumab, trastuzumab, atezolizumab, canakinumab, combinations thereof, and the like.

In embodiments, paclitaxel and/or paclitaxel derivatives may be used as the therapeutic agent. Paclitaxel may have various forms, referred to herein as "polymorphs," including amorphous paclitaxel, crystalline paclitaxel, sometimes referred to as crystalline paclitaxel dihydrate, and/or anhydrous paclitaxel, or mixtures thereof.

In accordance with the present disclosure, the polymorph form of paclitaxel utilized in forming the therapeutic layer may be varied by the aqueous composition, the solvent polarity and the composition of protic and aprotic solvents utilized in the solvent system to form the solution for applying the therapeutic layer. For example, paclitaxel dissolved and then dried from 10% v/v water in methanol will yield a predominantly crystalline paclitaxel dihydrate layer, while the same paclitaxel dissolved and then dried from non-polar solvent dichloromethane will yield a predominantly amorphous layer.

The crystallinity of the paclitaxel will impact its solubility in aqueous systems. Accordingly, the polymorph form of paclitaxel in the therapeutic layer may be adjusted and selected to provide a tailored release of therapeutic agent from the surgical buttress of the present disclosure. Although the drug in any form is hydrophobic, amorphous paclitaxel is more soluble in aqueous environments, and crystalline paclitaxel is less soluble in aqueous environments. Accordingly, in embodiments, more than one polymorphic form of paclitaxel may be used to provide implants that have multiple release profiles of paclitaxel. For example, surgical buttresses of the present disclosure having both amorphous paclitaxel and crystalline paclitaxel (dihydrate or anhydrous) thereon may release a bolus of therapeutic agent upon implantation (resulting primarily by amorphous paclitaxel dissolution), while also slowly releasing the therapeutic agent (resulting primarily by crystalline paclitaxel (dihydrate or anhydrous) dissolution).

In embodiments with no excipient, the amount of amorphous paclitaxel in the therapeutic layer forming at least one tab on the surgical buttress may be from 0% to about 100% by weight of the therapeutic layer, in embodiments from about 10% to about 90% by weight of the therapeutic layer, with the crystalline paclitaxel being present in amounts from about 0 to about 100% by weight of the therapeutic layer, in embodiments from about 90% to about 10% by weight of the therapeutic layer.

Surgical buttresses of the present disclosure may release amorphous paclitaxel in vivo over a period of time from about 18 hours to about 96 hours, in embodiments from about 24 hours to about 72 hours, and release the crystalline paclitaxel in vivo over a period of time from about 3 days to about 14 days, in embodiments from about 7 days to about 10 days.

In some embodiments, the therapeutic layer forming a tab at least one end of the surgical buttress may be formed of polymeric materials or other carrier components within the purview of those skilled in the art. In embodiments, such layers may include, for example, degradable materials such as those prepared from monomers such as glycolide, lactide, trimethylene carbonate, p-dioxanone, epsilon-caprolactone, and combinations thereof.

In other embodiments, regardless of whether the therapeutic agent is applied with or without some additional polymeric material to form the therapeutic layer, in addition to the therapeutic agents described above, therapeutic layers applied to the substrate material in forming a tab on a surgical buttress of the present disclosure may also include excipients to enhance both the ability of the therapeutic agent to adhere to the surgical buttress, as well as to modify the elution of the therapeutic agent from the surgical buttress.

In embodiments, suitable excipients which may be combined with a therapeutic agent to form the therapeutic layer include surfactants such as, but not limited to, cyclodextrins such as 2-hydroxypropyl-beta-cyclodextrin and methyl-β-cyclodextrin, sodium dodecyl sulfate, octyl glucoside, and sorbitan fatty acid esters such as sorbitan monooleate, sorbitan monolaurate and polyethoxylated fatty acid esters of sorbitan, sometimes referred to herein as polysorbates, including those sold under the name TWEEN™. Examples of such polysorbates include polysorbate 80 (TWEEN™ 80), polysorbate 20 (TWEEN™ 20), polysorbate 60 (TWEEN™ 60), polysorbate 65 (TWEEN™ 65), polysorbate 85 (TWEEN™ 85), combinations thereof, and the like. In embodiments, low molecular weight poly(ethylene glycol)s may be added as an excipient, either alone or in any combination with any of the other above excipients.

In other embodiments, suitable excipients may include salts such as sodium chloride and/or other materials such as urea, oleic acid, citric acid, and ascorbic acid. In yet other embodiments, the excipient may be a stabilizer such as butylated hydroxytoluene (BHT) or butylated hydroxyanisole (BHA).

Still other suitable excipients include polyhydric alcohols such as D-sorbitol, mannitol, combinations thereof, and the like.

In some embodiments, excipients which are hydrotropes may be included in the therapeutic layers of the present disclosure. These materials attract water into the therapeutic layer, which may enhance its degradation and resulting release of the therapeutic agent from the therapeutic layer.

In embodiments, the therapeutic agent(s), carrier component(s) and/or excipient(s) may be in a solution for application to a surgical buttress of the present disclosure. Any suitable solvent may be used to form such a solution. Suitable solvents for forming such a solution include any pharmaceutically acceptable solvents including, but not limited to, saline, water, alcohol, acetone, dimethyl sulfoxide, ethyl acetate, N-methylpyrrolidone, combinations thereof, and the like. Methods for forming such solutions are within the purview of those skilled in the art and include, but are not limited to, mixing, blending, sonication, heating, combinations thereof, and the like.

In embodiments, by selecting different solvent systems, different dissolution rates of the therapeutic agent(s) may be achieved due to different therapeutic agent morphologies and degrees of crystallinity that occur based upon the solvent used in forming the solution including the therapeutic agent(s).

In embodiments, the therapeutic agent(s), any carrier component(s), and/or any excipient(s) may be applied to the surgical buttress of the present disclosure by a needle deposition process. As noted above, in embodiments the therapeutic agent is in a solution, which is then applied to a surgical buttress of the present disclosure.

In embodiments, the therapeutic agent(s), any carrier component(s), and/or any excipient(s) may be applied to the medical device of the present disclosure prior to affixing the surgical buttress to some other medical apparatus. For example, in the case of a surgical buttress, the surgical buttress may be coated in accordance with the present disclosure prior to its attachment to a surgical stapler.

In embodiments, additional outer layers may be applied over a therapeutic agent coating layer on a surgical buttress of the present disclosure. Such additional layers, in embodiments, may be non-permeable, semi-permeable, or porous, to permit adjustment of the rate of release of a therapeutic agent from the therapeutic agent coating layer on a surgical buttress of the present disclosure.

Suitable materials for forming an outer layer on a surgical buttress include, for example, degradable materials such as those prepared from monomers such as glycolide, lactide, trimethylene carbonate, p-dioxanone, epsilon-caprolactone, and combinations thereof. In embodiments, suitable materials for forming an outer layer on a surgical buttress include, for example, phosphorylcholine polymers.

In accordance with the present disclosure, the therapeutic layer, including the therapeutic agent(s), solvent(s), any carrier component(s), and/or any excipient(s), is applied so that an adequate amount of therapeutic agent(s) is deposited and stays robustly attached to the surgical buttress, forming a tab on at least one end thereof.

After application, the solvent from the coating solution may be driven off by methods within the purview of those skilled in the art. For example, solvent evaporation may be facilitated by heat, gas flow, time, reduced pressure, combinations thereof, and the like, to increase the accuracy of drug deposition on the medical device. Moreover, this assisted evaporation of solvent may be applied to the whole surface of the surgical buttress, partially to only a portion of the surface of the medical device, or just around the deposition instrument (e.g., a needle tip).

Driving off the solvent leaves the therapeutic agent and any carrier component and/or excipient behind to form the therapeutic layer on the surgical buttress.

In accordance with the present disclosure, the process may be repeated, such that multiple passes can be made so that the surface the surgical buttress has the desired amount of therapeutic agent for administering a dose of the therapeutic agent. In embodiments, repeating the process described above results in the deposition of multiple layers such that the overall therapeutic layer on the buttress is very uniform and robust, and adheres to the surgical buttress material very well. This is in contrast to other processes, such as dip coating and other similar coating methods, which lack both the robustness and adherence of the coatings/layers produced in accordance with the present disclosure.

The process is designed in such a way that it leverages the capillary action of the fabric on which the drug is dispensed for coating. The speed and rate of dispersion are appropriately controlled to produce the desired coatings. Between coatings, the process may have pre-determined pauses to ensure each coat has the proper time to dry before more therapeutic agent is deposited as a next layer.

Utilizing the processes of the present disclosure, there is limited drug loss during the different stages of the process. This is beneficial in terms of isolating the therapeutic agent to areas where it is intended to stay, and cost savings in terms of the amount of therapeutic agent being used.

The process is very efficient from a manufacturing aspect as well. Using the process of the present disclosure, one can coat directly on the surgical buttress rather than coat on cartridge and anvil assemblies, which saves with respect to material handling, labor costs and quality related costs. Moreover, it is much safer for the operators. For example, the process is developed such that it is better than spray coating which can be very hazardous for operators running the process. A normal air flow hood would suffice for operating this process safely. Also, an isolator is not needed for this process which makes it very ergonomic for long term manufacturing.

The process is also designed such that it has the capability to deposit drug on specific areas on the device with high precision. Certain sections of the surface of the surgical buttress can be left non-coated by design to improve the performance of the surgical buttress, for instance better tissue healing around the staple line. In addition, varying amounts of therapeutic agent(s) may be applied to different areas of the surgical buttress, thereby creating concentration gradients of the therapeutic agent(s) on the surgical buttress and/or focused application of therapeutic agent(s) from selected portions of the surgical buttress.

In embodiments, multiple layers of therapeutic agents can be deposited on the surgical buttress with ease. In some cases, different therapeutic agents are applied in different layers. Different therapeutic benefits can thus be combined on one surgical buttress by using the multiple layers. In other embodiments, different therapeutic agents can be deposited on different areas on the surface of the surgical buttress, e.g., one therapeutic agent can be applied in one region/area, and a different therapeutic agent can be applied to a different region/area.

After formation, surgical buttresses of the present disclosure may possess the therapeutic agent in the coated buttress thereon in amounts from about 0.1% to about 50% by weight of the coated buttress, in embodiments from about 1% to about 10% by weight of the coated buttress. While excipients are not required, where present, non-polymeric excipients may be present in an amount from about 0.01% to about 80% by weight of the coated buttress, in embodiments from about 1% to about 11% by weight of the coated buttress. In other embodiments, where present, polymeric excipients may be present in an amount from about 0.014% to about 14% by weight of the coated buttress, in embodiments from about 5% to about 15% by weight of the coated buttress.

After formation, surgical buttresses of the present disclosure may possess the therapeutic agent in the therapeutic layer forming a tab thereon in amounts from about 0.01% to about 100% by weight of the therapeutic layer, in embodiments from about 1% to about 75% by weight of the therapeutic layer. While excipients are not required, where present, non-polymeric excipients may be present in an amount from about 1% to about 99% by weight of the therapeutic layer, in embodiments from about 8.5% to about 79.4% by weight of the therapeutic layer, and most preferably in embodiments from 9.5% to about 15%. In embodiments, where present, polymeric excipients may be present in an amount from about 1% to about 99% by weight of the therapeutic layer, in embodiments from about 5% to about 15% by weight of the therapeutic layer.

A therapeutic layer having both a therapeutic agent and non-polymeric excipients may have a thickness from about 13 nm to about 2.9 µm, in embodiments from about 25 nm to about 100 nm.

A therapeutic layer having both a therapeutic agent and polymeric excipients may have a thickness from about 2 nm to about 1.1 µm, in embodiments from about 30 nm to about 100 nm.

In other embodiments, the therapeutic layers may include little or no excipients, so very thin therapeutic layers may be applied to the substrate. This will maintain the porosity of the substrate. Such therapeutic layers may have a thickness from about 11 nm to about 218 nm, in embodiments from about 25 nm to about 75 nm.

Surgical buttresses of the present disclosure may release therapeutic agents therefrom over a period of time from about 18 hours to about 4 weeks, in embodiments from about 48 hours to about 2 weeks.

As noted above, the surgical buttress of the present disclosure may be used with any fixation device to further assist in sealing tissue. For example, surgical buttresses of the present disclosure may be used in conjunction with staples, tacks, clips, sutures, adhesives, combinations thereof, and the like.

In embodiments, a surgical buttress of the present disclosure is provided to reinforce and seal the lines of staples applied to tissue by a surgical stapling apparatus. The buttress may be configured into any shape, size, or dimension suitable to fit any surgical stapling, fastening, or firing apparatus.

Upon application to a site of bleeding tissue, the surgical buttress of the present disclosure may affect hemostasis of said tissue. As used herein, the term "hemostasis" means the arrest of bleeding.

In addition to providing hemostasis at the site of application of the surgical buttress, the surgical buttresses of the present disclosure may also provide for treatment of tissue with the therapeutic agent at both the site of implantation and elsewhere in the body.

It will be understood that various modifications may be made to the embodiments disclosed herein. Therefore, the above description should not be construed as limiting, but merely as an exemplification of preferred embodiments. Those skilled in the art will envision other modifications within the scope and spirit of the present disclosure. Such modifications and variations are intended to come within the scope of the following claims.

What is claimed is:

1. A surgical stapling device, comprising:
   an end effector including an anvil jaw member and a cartridge jaw member pivotally coupled to one another, the anvil jaw member and the cartridge jaw member being relatively movable such that the end effector is movable between an open position and a clamped position;
   a buttress attached to the cartridge jaw member, the buttress having a distal portion, a central portion configured to be penetrated by staples housed in the cartridge jaw member, and a proximal portion; and
   the distal portion comprising a first tab including a therapeutic agent as a coating, the proximal portion comprising a second tab including a therapeutic agent as a coating,
   wherein the central portion of the buttress is non-coated.

2. The surgical stapling device of claim 1, wherein a second buttress is attached to the anvil jaw member, the second buttress having a distal portion, a proximal portion, and a central portion configured to be penetrated by the staples, at least one of the distal portion and the proximal portion of the second buttress having a therapeutic agent thereon.

3. The surgical stapling device of claim 2, wherein the distal portion of the second buttress comprises a first tab including a therapeutic agent as a coating, and the proximal portion of the second buttress comprises a second tab including a therapeutic agent as a coating,
   wherein the central portion of the second buttress is non-coated.

4. The surgical stapling device of claim 2, wherein the second buttress is attached to the anvil jaw member by at least one suture.

5. The surgical stapling device of claim 1, wherein each of said therapeutic agents is any combination of amino acids, peptides, polypeptides, proteins, polysaccharides, muteins, immunoglobulins, antibodies, cytokines, blood clotting factors, hemopoietic factors, interleukins (1 through 18), interferons, erythropoietin, nucleases, tumor necrosis factor, colony stimulating factors, insulin, anti-tumor agents and tumor suppressors, blood proteins, fibrin, thrombin, fibrinogen, synthetic thrombin, synthetic fibrin, synthetic fibrinogen, gonadotropins, hormones and hormone analogs, vaccines, somatostatin, antigens, blood coagulation factors, growth factors, bone morphogenic proteins, TGF-B, protein inhibitors, protein antagonists, protein agonists, nucleic acids, such as antisense molecules, DNA, RNA, RNAi, oligonucleotides, polynucleotides, cells, viruses, anti-inflammatory agents, anti-bacterial agents, antimicrobial agents, and ribozymes.

6. The surgical stapling device of claim 1, wherein each of said therapeutic agents is a chemotherapy drug.

7. The surgical stapling device of claim 6, wherein the chemotherapy drug is any combination of paclitaxel and derivatives thereof, docetaxel and derivatives thereof, abraxane, tamoxifen, cyclophosphamide, actinomycin, bleomycin, dactinomycin, daunorubicin, doxorubicin, doxorubicin hydrochloride, epirubicin, mitomycin, methotrexate, fluorouracil, gemcitabine, gemcitabine hydrochloride, carboplatin, carmustine, methyl-CCNU, cisplatin, etoposide, camptothecin and derivatives thereof, phenesterine, vinblastine, vincristine, goserelin, leuprolide, interferon alfa, retinoic acid, nitrogen mustard alkylating agents, piposulfan, vinorelbine, irinotecan, irinotecan hydrochloride, vinblastine, pemetrexed, sorafenib tosylate, everolimus, erlotinib hydrochloride, sunitinib malate, capecitabine oxaliplatin, leucovorin calcium, bevacizumab, cetuximab, ramucirumab, trastuzumab, atezolizumab, canakinumab, and combinations thereof.

8. The surgical stapling device of claim 1, wherein the therapeutic agent is combined with an excipient including a surfactant, a salt, an acid, a stabilizer, a polyhydric alcohol, a hydrotrope, a low molecular weight poly(ethylene glycol) or any combination thereof.

9. The surgical stapling device of claim 8, wherein the surfactant is a cyclodextrin, sodium dodecyl sulfate, octyl glucoside, a sorbitan fatty acid ester, or combinations thereof.

10. The surgical stapling device of claim 8, wherein the salt includes sodium chloride.

11. The surgical stapling device of claim 8, wherein the acid includes oleic acid, citric acid, ascorbic acid, or combinations thereof.

12. The surgical stapling device of claim 8, wherein the stabilizer includes butylated hydroxytoluene.

13. The surgical stapling device of claim 8, wherein the polyhydric alcohol includes D-sorbitol, mannitol, or combinations thereof.

14. The surgical stapling device of claim 1, wherein the buttress is attached to the cartridge jaw member by at least one suture.

15. A method for treating tissue comprising stapling tissue with the surgical stapling device of claim 1.

16. A surgical stapling device, comprising:
an end effector including an anvil jaw member and a cartridge jaw member pivotally coupled to one another, the anvil jaw member and the cartridge jaw member being relatively movable such that the end effector is movable between an open position and a clamped position;
a buttress attached to the cartridge jaw member, the buttress having a distal portion, a central portion configured to be penetrated by staples housed in the cartridge jaw member, and a proximal portion; and
the distal portion comprising a first tab including a chemotherapy drug as a coating, the proximal portion including a second tab including a chemotherapy drug as a coating,
wherein the central portion of the buttress is non-coated.

17. The surgical stapling device of claim 16, wherein a second buttress is attached to the anvil jaw member, the second buttress having a distal portion, a proximal portion, and a central portion configured to be penetrated by the staples, at least one of the distal portion and the proximal portion of the second buttress having a chemotherapy drug thereon.

18. The surgical stapling device of claim 17, wherein the distal portion of the second buttress comprises a first tab including a chemotherapy drug as a coating, and the proximal portion of the second buttress comprises a second tab including a chemotherapy drug as a coating, and wherein the central portion of the second buttress is non-coated.

19. The surgical stapling device of claim 17, wherein each of said chemotherapy drugs is any combination of paclitaxel and derivatives thereof, docetaxel and derivatives thereof, abraxane, tamoxifen, cyclophosphamide, actinomycin, bleomycin, dactinomycin, daunorubicin, doxorubicin, doxorubicin hydrochloride, epirubicin, mitomycin, methotrexate, fluorouracil, gemcitabine, gemcitabine hydrochloride, carboplatin, carmustine, methyl-CCNU, cisplatin, etoposide, camptothecin and derivatives thereof, phenesterine, vinblastine, vincristine, goserelin, leuprolide, interferon alfa, retinoic acid, nitrogen mustard alkylating agents, piposulfan, vinorelbine, irinotecan, irinotecan hydrochloride, vinblastine, pemetrexed, sorafenib tosylate, everolimus, erlotinib hydrochloride, sunitinib malate, capecitabine oxaliplatin, leucovorin calcium, bevacizumab, cetuximab, ramucirumab, trastuzumab, atezolizumab, canakinumab, and combinations thereof.

* * * * *